United States Patent
Sakata et al.

(10) Patent No.: US 7,354,947 B2
(45) Date of Patent: Apr. 8, 2008

(54) ISOTHIAZOLOANTHRONES, ISOXAZOLOANTHRONES, ISOINDOLANTHRONES AND DERIVATIVES THEREOF A JNK INHIBITORS AND COMPOSITIONS AND METHODS RELATED THERETO

(75) Inventors: Steven T. Sakata, San Diego, CA (US); Heather K. Raymon, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 11/159,592

(22) Filed: Jun. 22, 2005

(65) Prior Publication Data

US 2006/0004080 A1 Jan. 5, 2006

Related U.S. Application Data

(62) Division of application No. 10/071,390, filed on Feb. 7, 2002, now Pat. No. 6,987,184.

(60) Provisional application No. 60/269,013, filed on Feb. 15, 2001.

(51) Int. Cl.
*A61K 31/403* (2006.01)
*C07D 209/80* (2006.01)

(52) U.S. Cl. ........................ 514/410; 548/420

(58) Field of Classification Search ........... 514/410; 548/420

See application file for complete search history.

(56) References Cited

U.S. PATENT DOCUMENTS

| 3,095,415 A | 6/1963 | Staeuble |
|---|---|---|
| 3,522,263 A | 7/1970 | Guenthard |
| 6,162,613 A | 12/2000 | Su et al. |

FOREIGN PATENT DOCUMENTS

| EP | 0 208 211 | 1/1987 |
|---|---|---|
| FR | 2 024 807 A | 9/1970 |
| FR | 2 167 626 A | 8/1973 |
| FR | 2 336 708 A | 7/1977 |
| FR | 2 401 915 A | 3/1979 |
| GB | 355597 | 11/1929 |
| GB | 355597 | * 11/1999 |
| WO | WO 99/53927 | 10/1999 |
| WO | WO 99/57253 | 11/1999 |
| WO | WO 00/35909 | 6/2000 |
| WO | WO 00/64872 | 11/2000 |
| WO | WO 00/75118 | 12/2000 |
| WO | WO 01/12621 A1 | 2/2001 |
| WO | WO 02/085396 | 10/2002 |

OTHER PUBLICATIONS

Ames et al., "An integrated concept of amebicidal action: electron transfer and oxy radicals", *Free Radical Biol. Med.*, 3(2):85-96 (Chemabs Online) (1987).

Aspenstrom et al., "Two GTPases, Cdc42 and Rac, bind directly to a protein implicated in the immunodeficiency disorder Wiskott-Aldrich syndrome", *Curr. Biol.* 6:70-77 (1996).

Chen et al., "Activation and inhibition of the AP-1 complex in human breast cancer cells", *Mol. Carcinogenesis* 15:215-226 (1996).

Deacon et al., "MEK kinase 3 directly activates MKK6 and MKK7, specific activators of the p38 and c-Jun NH2-terminal kinases", *J. Biol. Chem.* 274:16604-16610 (1999).

Dong et al., "Defective T cell differentiation in the absence of Jnk1", *Science* 282:2092-2095 (1998).

Faris et al., "Regulation of interleukin-2 transcription by inducible stabile expression of dominant negative and dominant active mitogen-activated protein kinase in Jurkat T cells", *J. Biol. Chem.* 271:27366-27273 (1996).

Galushko et al., "Derivatives of pyrazoloanthrone. 1. Reactivity of 2-aminopyrazoloanthrone", *Khim. Geterotsikl. Soedin.*, 7:956-61 (Chemabs Online) (1977).

Gum et al., "Regulation of 92 kDa type IV collagenase expression by the jun aminoterminal kinase- and the extracellular signal-regulated kinase-dependent signaling cascades", *Oncogene* 14:1481-1493 (1997).

Gvon et al., "Amino-amino tautomerism and intramolecular cyclization of 4,9-diamino-1, 10-anthraquinone-1-tosylimines", *Dokl. Akad. Nauk*, 334(4):465-8, (Chemabs Online) (1994).

(Continued)

*Primary Examiner*—Kamal A. Saeed
(74) *Attorney, Agent, or Firm*—Jones Day

(57) ABSTRACT

Isaothiazoloanthrones, isooxazoloanthrones, isoindolan-thrones, and derivatives thereof having the general formula:

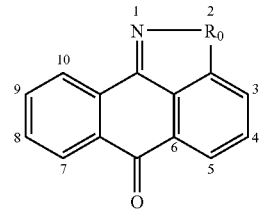

Figure 1:
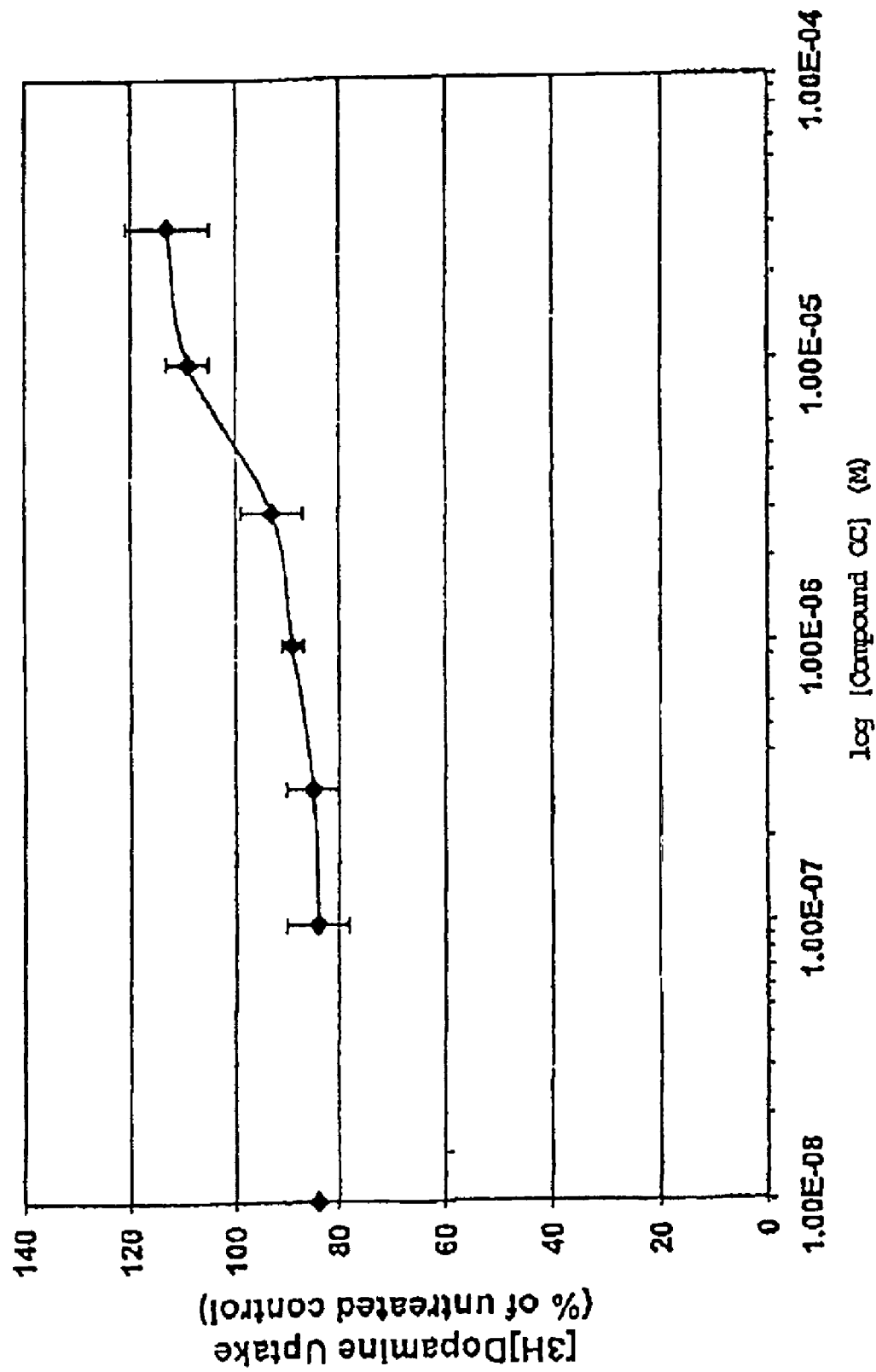

and pharmaceutically acceptable salts thereof, wherein $R_0$ is $-CH_2-$, $-SO-$, $-O-$, $-SO_2-$, or $-S-$; compositions comprising the iazoloanthrones, isoox-azoloanthrones, isoindolanthrones, and derivatives thereof; and methods for treating or preventing a disorder alleviated by inhibiting Jun N-terminal kinase (JNK) by administering the isaothiazoloanthrones, isooxazoloanthrones, isoindolanthrones, and derivatives thereof are described herein.

4 Claims, 1 Drawing Sheet

OTHER PUBLICATIONS

Gwon et al., "Direct animation of 6H-anthra(9,1-cd)isothiazol-6-one 2,2-dioxides", *Dokl. Akad. Nauk*, 359:357-61, Case No. 130:153598d (1998) (Abstract).

Han et al., "Jun N-terminal kinase in rheumatoid arthritis", *J. Pharm. Exp. Therap.* 291:1-7 (1999).

Hartley et al., "Characteristics of the interaction of anthrapyrazole anticancer agents with deoxyribonucleic acids: structural requirements for DNA binding, intercalation, and photsensitization", *Mol. Pharmacol.*, 33(3):265-71 (Chemabs Online) (1988).

Herdegen et al., "Lasting N-terminal phosphorylation of c-Jun and activation of c-Jun N-terminal kinases after neuronal injury", *J. Neurosci.* 18:5124-5135 (1998).

Hibi et al., "Identification of an oncoprotein- and UV-responsive protein kinase that binds and potentiates the c-Jun activation domain", *M. Genes Dev.* 7:2135-2148 (1993).

Hirosumi et al., "A central role for JNK in obesity and insulin resistance", *Letters to Nature* 420:333-336 (2002).

Ishizuka et al., "Mast cell tumor necrosis factor alpha production is regualted by MEK kinases", *Proc. Nat. Acad. Sci. USA* 94:6358-6363 (1997).

Ivanova et al., "IPS investigation of electronic structure of pyrazolanthrone and its derivatives", *Poverkhnost* 4-5:193-201 (Chemabs Online) (1997).

JP 60 028,454, Mitsubishi Chemical Industries Co., Ltd., Case No. 102: 205411f (Abstract).

JP 60 092,355, Mitsubishi Chemical Industries Co., Ltd., Case No. 103: 143360y (Abstract).

JP 60 250,052, Mitsubishi Chemical Industries Co., Ltd., Case No. 104: 208328m (Abstract).

Judson, "The anthrapyrazoles: a new class of compounds with clinical activity in breast cancer", *Semin. Oncol.* 19(6):687-94 (Chemabs Online) (1992).

Karin et al., "AP-1 function and regulation", *Curr Opin Cell Biol* 9:240-246 (1997).

Kiyooka et al., "Photochemical Intramolecular Cyclization Reactions of Acylgermanes", Jr. *J. Org. Chem.* 55, 5562-4 (1990).

Lange-Carter et al., "A divergence in the MAP kinase regulatory network defined by MEK kinase and Raf.", *Science* 260:315-319 (1993).

Li et al., "Blocked signal transduction to the ERK and JNK protein kinases in anergic CD4+ T cells", *Science* 271:1272-1276 (1996).

Li et al., "The Ras-JNK pathway is involved in shear-induced gene expression", *Mol. Cell. Biol.* 16:5947-5954 (1996).

Lin et al., "Indentification of a dual specificity kinase that activates the Jun kinases and p38-Mpk2", *Science* 268:286-289 (1995).

Maj et al, "PNU 151774E protects against kainate-induced status epilepticus and hippocampal lesions in the rat", *Eur. J. Pharm.* 359:27-32, 1992.

Manning et al., "Transcription inhibitors in inflammation", *Exp. Opin. Invest. Drugs* 6:555-567 (1997).

Maroney et al., "Motoneuron apoptosis is blocked by CEP-1347 (KT 7515), a novel inhibitor of the JNK signaling pathway", *J. Neurosci.* 18:104-111 (1998).

Mielke et al., "JNK and p38 stresskinases—degenerative effectors of signal-transduction-cascades in thenervous system", *Prog. Neurobiol.* 61:45-60 (2000).

Milne et al., "p53 is phosphorylated in vitro and in vivo by an ultraviolet radiation-induced protein kinase characteristic of the c-Jun kinase, JNK1", *J. Biol. Chem.* 270:5511-5518 (1995).

Mohit et al., "p493F12 kinase: a novel MAP kinase expressed in a subset of neurons in the human nervous system", C.A. *Neuron* 14:67-75 (1995).

Nishina et al., "Impaired CD28-mediated interleukin 2 production and proliferation in stress kinase SAPK/ERK1 kinase (SEK1)/mitogen-activated protein kinase kinase 4 (MKK4)-deficient T lymphocytes", *J. Exp. Med.*, 186:941-953 (1997).

Okamoto et al., "Selective activation of the JNK/AP-1 pathway in Fas-mediated apoptosis of rheumatoid arthritis synoviocytes", *Arth & Rheum* 40: 919-926 (1997).

Pombo et al., "The stress-activated protein kinases are major c-Jun amino-terminal kinases activated by ischemia and reperfusion", *J. Biol. Chem.* 26 :26546-26551 (1994).

Raitano et al., "the Bcr-Abl leukemia oncogene activates Jun kinase and requires Jun for transformation", *Proc. Nat. Acad. Sci. USA* 92:11746-11750 (1995).

Richards et al, *Am. J. Physiol*, 271:2, Pt 1, L267-76 (1996).

Sabapathy et al., "JNK2 is required for efficient T-cell activation and apoptosis but not for normal lymphocyte development", *Curr Biol.* 9:116-125 (1999).

Saporita et al., "CEP-1347/KT-7515, an inhibitor of c-jun N-terminal kinase activation, attenuates the 1-methyl-4-phenyl tetrahydropyridine-mediated loss of nigrostriatal dopaminergic neurons In vivo", *J Pharmacol Exp Ther.* 288(2):421-7 (1999).

Saporito et al., Preservation of cholinergic activity and prevention of neuron death by CEP-1347/KT-7515 following excitotoxic injury of the nucleus basalis magnocellularis:, *Neuroscience* 86:461-472 (1998).

Shah et al., Thiocyanation of 1-aminoanthraquinones, Indian J. Chem. 14B: 625-626. Case No. 86: 121031v (1976) (Abstract).

Showalter et al., "5-(Aminoalkyl)amino!-substituted anthra'1,9-cd!pyrazol-6(2H)-ones as novel anticancer agents. Synthesis and biological evaluation", *J. Med. Chem.*, 27(3):253-5 (1984).

Showalter et al., "Anthrapyrazole anticancer agents. Synthesis and structure-activity relationships against murine leukemias" J. Med. Chem., 30(1):121-31 (Chemabs Online) (1987).

Singh, et al., "Reactions of 2,2'-ethylenebis(anthrapyrazolone)", *Indian J. Chem.* Sect. B, 16B(2):100-2 (Chemabs Online) (1978).

Sokolyuk et al., "Synthesis and photochemical properties of peri-phenoxy derivatives of 6H-anthra'1,9-cd!-6-pyrazolone (pyrazole anthrone)", 28(10):2193-200 (Chemabs Online) 1992.

Spiegelman et al., "Regulation of Adipocyte Gene Expression in Differentiation and Syndromes of Obesity Diabetes", *J. of Biol. Chem.* 268:6823-6826 (1993).

Su et al., "JNK is involved in signal integration during costimulation of T lymphocytes", *Cell* 77:727-736 (1994).

Swantek et al., "Jun N-terminal kinase/stress-activated protein kinase (JNK/SAPK) is required for lipopolysaccharide stimulation of tumor necrosis factor alpha (TNF-alpha) translation: glucocorticoids inhibit TNF-alpha translation by blocking JNK/SAPK", *Mol. Cell. Biol.* 17:6274-6282 (1997).

Szabo et al., "Altered cJUN expression: an early event in human lung carcinogenesis"*Cancer Res.* 56:305-315 (1996).

Teramoto et al., "Signaling from the small GTP-binding proteins Rac1 and Cdc42 to the c-Jun N-terminal kinase/stress-activated protein kinase pathway. A role for mixed lineage kinase 3/protein-tyrosine kinase 1, a novel member of the mixed lineage kinase family", *J. Biol. Chem.* 271:27225-27228 (1996).

Tournier et al., "Mitogen-activated protein kinase kinase 7 is an activator of the c-Jun NH2-terminal kinase", *Proc. Nat. Acad. Sci. USA* 94:7337-7342 (1997).

Whitmarsh et al., "Transcription factor AP-1 regulation by mitogen-activated protein kinase signal transduction pathways", *J. Mol. Med.* 74:589-607 (1996).

Winter et al, *Arthritis and Rheumatism* 9(3):394-404, 1966: Weichman et al, *Pharmacological Methods in the Control of Infamation*, Chang and Lewis Eds., Alan R. Liss, Inc. Publ., New York, 1989.

Yan et al., "Activation of stress-activated protein kinase by MEKK1 phosphorylation of its activator SEK1", *Nature* 372:798-800 (1994).

Yang et al., "Absence of excitotoxicity-induced apoptosis in the hippocampus of mice lacking the Jnk3 gene", *Nature* 389:865-870 (1997).

Yang et al., "Differentiation of CD4+ T cells to Th1 cells requires MAP kinase JNK2", *Immunity,* 9:575-585 (1998).

Yin et al., "Tissue-specific pattern of stress kinase activation in ischemic/reperfused heart and kidney", *J. Biol. Chem.* 272:19943-19950 (1997).

* cited by examiner

ISOTHIAZOLOANTHRONES, ISOXAZOLOANTHRONES, ISOINDOLANTHRONES AND DERIVATIVES THEREOF A JNK INHIBITORS AND COMPOSITIONS AND METHODS RELATED THERETO

This application is a Divisional of U.S. patent application Ser. No. 10/071,390 filed Feb. 7, 2002 now U.S. Pat. No. 6,987,184, which claims benefit of U.S. Provisional Application No. 60/269,013, filed Feb. 15, 2001, each Application being incorporated by reference herein in its entirety.

1. FIELD OF THE INVENTION

This invention is generally directed to isothiazoloanthrones, isoxazoloanthrones, isoindoianthrones, and derivatives thereof; compositions comprising the isothiazoloanthrones, isoxazoloanthrones, isoindolanthrones, and derivatives thereof; and methods for treating or preventing a disease or disorder alleviated by inhibiting Jun N-terminal kinase, (JNK) comprising administering an effective amount of the isothiazoloanthrones, isoxazoloanthrones, isoindolanthrones, or derivatives thereof to a patient in need thereof

2. BACKGROUND OF THE INVENTION

The Jun N-terminal kinase (JNK) pathway is activated by exposure of cells to environmental stress or by treatment of cells with pro-inflammatory cytokines. Targets of the JNK pathway include the transcription factors c-jun and ATF2 (Whitmarsh A. J., and Davis R. J. *J. Mol. Med.* 74:589-607, 1996). These transcription factors are members of the basic leucine zipper (bZIP) group that bind as homo- and heterodimeric complexes to AP1 and AP-1-like sites in the promoters of many genes (Karin M., Liu Z. G. and Zandi E. *Curr Opin Cell Biol* 9:240-246, 1997). JNK binds to the N-terminal region of c-jun and ATF-2 and phosphorylates two sites within the activation domain of each transcription factor (Hibi M., Lin A., Smeal T., Minden k, Karin M. *Genes Dev.* 7:2135-2148, 1993; Mohit A. A., Martin M. H., and Miller C. A. *Neuron* 14:67-75, 199). Three JNK enzymes have been identified as products of distinct genes (Hibi et al, supra; Mohit et al., supra). Ten different isoforms of JNK have been identified. These represent alternatively spliced forms of three different genes: JNK1, JNK2, and JNK3. JNK1 and 2 are ubiquitously expressed in human tissues, whereas JNK3 is selectively expressed in the brain, heart, and testis (Dong, C., Yang, D., Wysk, M., Whitmarsh, A., Davis, R., Flavell, R. *Science* 270:1-4, 1998). Gene transcripts are alternatively spliced to produce four-JNK1 isoforms, four-JNK2 isoforms, and two-JNK3 isoforms. JNK1 and 2 are expressed widely in mammalian tissues, whereas JNK3 is expressed almost exclusively in the brain. Selectivity of JNK signaling is achieved via specific interactions of JNK pathway components and by use of scaffold proteins that selectively bind multiple components of the signaling cascade. JIP-1 (JNK-interacting protein-1) selectively binds the MAPK module, MLK→JNKK1→JNK. It has no binding affinity for a variety of other MAPK cascade enzymes. Different scaffold proteins are likely to exist for other MAPK signaling cascades to preserve substrate specificity.

JNKs are activated by dual phosphorylation on Thr-183 and Tyr-185. JNKK1 (also known as MKK 4) and JNKK2 (MKK7), two MAPKK level enzymes, can mediate JNK activation in cells (Lin A., Minden A., Martinetto H., Claret F.-Z., Lange-Carter C., Mercurio F., Johnson G. L., and Karin M. *Science* 268:286-289, 1995; Tournier C., Whitmarsh A. J., Cavanagh J., Barrett T., and Davis R. J. *Proc. Nat. Acad. Sci. USA* 94:7337-7342, 1997). JNKK2 specifically phosphorylates JNK, whereas JNKK1 can also phosphorylate and activate p38. Both JNKK1 and JNKK2 are widely expressed in mammalian tissues. JNKK1 and JNKK2 are activated by the MAPKKK enzymes, MEKK1 and 2 (Lange-Carter C. A., Pleiman C. M., Gardner A. M., Blumer K. J., and Johnson G. L., *Science,* 260:315-319, 1993; Yan M., Dai J. C., Deak J. C., Kyrakis J. M., Zon L. I., Woodgett J. R., and Templeton D. J., *Nature,* 372:798-781, 1994). Both MEKK1 and MEKK2 are widely expressed in mammalian tissues.

Activation of the JNK pathway has been documented in a number of disease settings, providing the rationale for targeting this pathway for drug discovery. In addition, molecular genetic approaches have validated the pathogenic role of this pathway in several diseases. For example, autoimmune and inflammatory diseases arise from the overactivation of the immune system. Activated immune cells express many genes encoding inflammatory molecules, including cytokines, growth factors, cell surface receptors, cell adhesion molecules, and degradative enzymes. Many of these genes are regulated by the JNK pathway, through activation of the transcription factors AP-1 and ATF-2, including TNFa, IL-2, E-selectin, and matrix metalloproteinases such as collagenase-1 (Manning A. M. and Mercurio F., *Exp Opin Invest Drugs,* 6: 555-567, 1997). Monocytes, tissue macrophages, and tissue mast cells are key sources of TNFa production. The JNK pathway regulates TNFa production in bacterial lipopolysaccharide-stimulated macrophages, and in mast cells stimulated through the FceRII receptor (Swantek J. L., Cobb M. H., Geppert T. D., *Mol. Cell. Biol.,* 17:6274-6282, 1997; Ishizuka, T., Tereda N., Gerwins, P., Hamelmann E., Oshiba A., Fanger G. R., Johnson G. L., and Gelfiand E. W., *Proc. Nat. Acad. Sci. USA,* 94:6358-6363, 1997). Inhibition of JNK activation effectively modulates TNFa secretion from these cells. The JNK pathway therefore regulates production of this key pro-inflammatory cytokine. Matrix metalloproteinases (MMPs) promote cartilage and bone erosion in rheumatoid arthritis, and generalized tissue destruction in other autoimmune diseases. Inducible expression of MMPs, including MMP-3 and MMP-9, type II and IV collagenases, are regulated via activation of the JNK pathway and AP-1 (Gum, R., Wang, H., Lengyel, E., Juarez, J., and Boyd, D., *Oncogene,* 14:1481-1493, 1997). In human rheumatoid synoviocytes activated with TNFa, IL-1, or Fas ligand the JNK pathway is activated (Han Z., Boyle D. L., Aupperle K. R., Bennett B., Manning A. M., Firestein G. S., *J. Pharm. Exp. Therap.,* 291:1-7, 1999; Okamoto K., Fujisawa K., Hasunuma T., Kobata T., Sumida T., and Nishioka K., *Arth & Rheum,* 40: 919, 1997). Inhibition of JNK activation results in decreased AP-1 activation and collagenase-1 expression (Han et al., supra). The JNK pathway therefore regulates MMP expression in cells involved in rheumatoid arthritis.

Inappropriate activation of T lymphocytes initiates and perpetuates many autoimmune diseases, including asthma, inflammatory bowel disease, and multiple sclerosis. The JNK pathway is activated in T cells by antigen stimulation and CD28 receptor co-stimulation and regulates production of the growth factor IL-2 and cellular proliferation (Su B., Jacinto E., Hibi M., Kallunki T., Karin M., Ben-Neriah Y. *Cell,* 77:727-736, 1994; Faris M., Kokot N., Lee L., and Nel A. E., *J. Biol. Chem.,* 271:27366-27373, 1996). Peripheral T cells from mice genetically deficient in JNKK1 show decreased proliferation and IL-2 production after CD28 co-stimulation and PMA/Ca2+ ionophore activation, providing important validation for the role of the JNK pathway in these cells (Nishina H., Bachmann M., Oliveria-dos-Santos A. J., et al., *J. Exp. Med.,* 186: 941-953, 1997). It is known that T cells activated by antigen receptor stimulation in the absence of accessory cell-derived co-stimulatory signals lose the capacity to synthesize IL-2, a state called clonal anergy. This is an important process by which autoreactive T cell populations are eliminated from the peripheral circulation. Of note, anergic T cells fail to activate the JNK pathway in response to CD3- and CD28-receptor co-stimulation, even though expression of the JNK enzymes is unchanged (Li W., Whaley C. D., Mondino A., and Mueller D. L., *Science* 271:1272-1276, 1996). Recently, the examination of JNK-deficient mice revealed that the JNK pathway plays a key role in T cell activation and differentiation to T helper 1 and 2 cell types. JNK 1 or JNK2 knockout mice develop normally and are phenotypically unremarkable. Activated naive CD4+ T cells from these mice fail to produce IL-2 and do not proliferate well (Sabapathy, K, Hu, Y, Kallunki, T, Schreiber, M, David, J-P, Jochum, W, Wagner, E, Karin, M,. *Curr Biol* 9:116-125, 1999). It is possible to induce T cell differentiation in T cells from these mice, generating Th1 cells (producers of IFN-g and TNFβ) and Th2 effector cells (producers of IL-4, IL-5, IL-6, IL-10, and IL-13). Deletion of either JNK1 or JNK2 in mice resulted in a selective defect in the ability of Th1 effector cells to express IFNg. This suggests that JNK1 and JNK2 do not have redundant functions in T cells and that they play different roles in the control of cell growth, differentiation, and death. The JNK pathway therefore, is an important point for regulation of T cell responses to antigen.

Cardiovascular disease (CVD) accounts for nearly one quarter of total annual deaths worldwide. Vascular disorders such as atherosclerosis and restenosis result from dysregulated growth of the vessel wall, restricting blood flow to vital organs. The JNK pathway is activated by atherogenic stimuli and regulates local cytokine and growth factor production in vascular cells (Yang, D D, Conze, D, Whitmarsh, A J, et al., *Immunity,* 9:575, 1998). In addition, alterations in blood flow, hemodynamic forces, and blood volume lead to JNK activation in vascular endothelium, leading to AP-1 activation and pro-atherosclerotic gene expression (Aspenstrom P., Lindberg U., and Hall A., *Curr. Biol.* 6:70-77, 1996). Ischemia and ischemia coupled with reperfusion in the heart, kidney, or brain results in cell death and scar formation, which can ultimately lead to congestive heart failure, renal failure, or cerebral dysfunction. In organ transplantation, reperfusion of previously ischemic donor organs results in acute leukocyte-mediated tissue injury and delay of graft function. The JNK pathway is activated by ischemia and reperfusion (Li Y., Shyy J., Li S., Lee J., Su B., Karin M., Chien S., *Mol. Cell. Biol.,* 16:5947-5954, 1996), leading to the activation of JNK-responsive genes and leukocyte-mediated tissue damage. In a number of different settings JNK activation can be either pro- or anti-apoptotic. JNK activation is correlated with enhanced apoptosis in cardiac tissues following ischemia and reperfusion (Pombo C M, Bonventre J V, Avruch J, Woodgett J R, Kyriakis J. M, Force T., *J. Biol. Chem.* 269:26546-26551, 1994).

Cancer is characterized by uncontrolled growth, proliferation and migration of cells. Cancer is the second leading cause of death with 500,000 deaths and an estimated 1.3 million new cases in the United States in 1996. The role of signal transduction pathways contributing to cell transformation and cancer is a generally accepted concept. The JNK pathway leading to AP-1 appears to play a critical role in cancer. Expression of c-jun is altered in early lung cancer and may mediate growth factor signaling in non-small cell lung cancer (Yin T., Sandhu G., Wolfgang C. D., Burrier A., Webb R. L., Rigel D. F. Hai T., and Whelan J., *J. Biol. Chem.* 272:19943-19950, 1997). Indeed, over-expression of c-jun in cells results in transformation, and blocking c-jun activity inhibits MCF-7 colony formation (Szabo E., Riffe M., Steinberg S. M., Birrer M. J., Linnnoila R. I., *Cancer Res.* 56:305-315, 1996). DNA-damaging agents, ionizing radiation, and tumor necrosis factor activate the JNK pathway. In addition to regulating c-jun production and activity, JNK activation can regulate phosphorylation of p53 and, thus, can modulate cell cycle progression (Chen T. K., Smith L. M., Gebhardt D. K., Birrer M. J., Brown P. H., *Mol. Carcinogenesis,* 15:215-226, 1996). The oncogene BCR-Abl, associated with t(9,22) Philadelphia chromosome translocation of chronic myelogenous leukemia, activates JNK and leads to transformation of hematopoietic cells (Milne D. M., Campbell L. E., Campbell D. G., Meek D. W., *J. Biol. Chem.* 270:5511-5518, 1995). Selective inhibition of JNK activation by a naturally occurring JNK inhibitory protein, called JIP-1, blocks cellular transformation caused by BCR-Abl expression (Raitano A. B., Halpern J. R., Hambuch T. M., Sawyers C. L., *Proc. Nat. Acad. Sci USA,* 92:11746-11750, 1995). Thus, JNK inhibitors may block transformation and tumor cell growth.

Stroke is the $3^{rd}$ leading cause of death and a leading cause of disability in the U.S. Stroke, along with neurodegenerative diseases, such as Alzheimer's (AD) and Parkinson's disease (PD) impose a huge burden on the health care industry by impacting the quality of life of those affected. Loss of neuronal cell populations in stroke, AD, or PD underlies the motor and/or cognitive deficiencies in these patient populations. The mechanism by which neurons die in response to insult has not been fully elucidated; however, activation of the JNK pathway has been implicated as a major signaling pathway for neuronal apoptosis. (For review see Mielke K. and Herdegen T. *Prog. Neurobiol.* 61:45-60, 2000). A variety of insults have been shown to activate the JNK pathway in neurons. For example, activation of JNKs and phosphorylation of c-jun has been shown in brains of rats subjected to axotomy or ischemia with reperfusion, where neuronal cell loss was observed (Herdegen T., Claret F.-X., Kallunki, T., Matin-Villalba A., Winter C., Hunter T. and Karin M. *J. Neurosci.* 18:5124-5135, 1998). Further, inhibition of the mixed lineage kinase (MLK)-3, an upstream kinase in the JNK pathway, by CEP-1347 prevented motoneuron cell death following growth factor withdrawal in vitro (Maroney A. C., Glicksman M. A., Basma A. N., Walton K. M., Knight Jr. E., Murphy C. A., Bartlett B. A., Finn J. P., Angeles T., Matsuda Y., Neff N. T. and Dionne C. A., *J. Neurosci.* 18:104-111, 1998), protected cholinergic neurons following excitotoxic injury of the nucleus basalis magnocellularis (Saporito M. S., Brown, E. R., Miller M. S., Murakata C., Neff N. H., Vaught J. L., and Carswell S. *Neuroscience* 86:461-472, 1998), and blocked the degeneration of midbrain dopamine neurons in mice treated with the neurotoxin, 1-methyl-4-phenyl tetrahydropyridine (Saporito M. S., Brown E. M., Miller M. S. and Carswell S. *J. Pharm. Exp. Ther.,* 1999). While JNK1 and JNK2 enzymes have a widespread tissue distribution, JNK3 is selectively expressed in brain and to a lesser extent in the heart and testis (Dong C., Yang D., Wysk M., Whitmarsh A., Davis R., and Flavell R. *Science* 270:1-4, 1998). Because of this restricted distribution, JNK3 may be the prevailing kinase mediating neuronal apoptosis. In support of JNK3's involvement in neuronal apoptosis, disruption of the gene encoding JNK3 in mice confers resistance to kainic acid-induced seizures and subsequent hippocampal neuronal cell death (Yang D. D., Kuan C.-Y., Whitmarsh A. J., Rincon M., Zheng T. S., Davis R. J., Rakic P. and Flavell R. A. *Nature* 389:865-870, 1997). Mounting evidence points to a role for the JNK pathway in neuronal apoptosis. Therefore, selective JNK inhibitors should prevent neuronal cell death observed in disorders and diseases of the CNS.

Accordingly, there is a need in the art for treating or preventing a disease associated with modulation of JNK, compositions comprising modulators of JNK, and methods of modulating INK and treating or preventing a disorder that is alleviated by modulation of JNK. The present invention fulfills these needs, and provides further related advantages.

Citations or identification of any reference in Section 2 of this application is not to be construed that such reference is prior art to the present application.

3. SUMMARY OF THE INVENTION

The present invention encompasses novel compounds having the general Formula:

(I)

or pharmaceutically acceptable salts thereof, being (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position;

the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

(a)

(b)

(c)

(d)

(e)

(f)

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

In one embodiment, the first and second substituent of compounds of Formula I, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

(a)

(b)

(c)

(d)

(e)

[Structure (e): acetyl group with N(R₃)(R₄)]

(f)

[Structure (f): methylsulfonyl group with N(R₃)(R₄)]

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

The present invention further provides novel compounds of the Formula:

(II)

[Structure II: tetracyclic compound with isothiazole S(=O)=N fused ring system, numbered positions 1-10, with ketone at position 6]

or pharmaceutically acceptable salts thereof, being (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b) (c), (d), (e), or (f):

(a)

[Structure (a): —N(R₃)(R₄)]

(b)

[Structure (b): —NH—(alkyl)—N(R₃)(R₄)]

(c)

[Structure (c): amide —N(H)—C(=O)—R₅]

(d)

[Structure (d): sulfonamide —N(H)—S(=O)₂—R₅]

(e)

[Structure (e): acetyl —N(R₃)(R₄) with C(=O)CH₃]

(f)

[Structure (f): methylsulfonyl —N(R₃)(R₄)]

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, and di-alkylaminoalkyl; and R₅ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, di-alkylaminoalkyl.

In one embodiment, the first and second substituent of compounds of Formula II, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

(a)

[Structure (a): —N(R₃)(R₄)]

(b)

[Structure (b): —NH—(alkyl)—N(R₃)(R₄)]

(c)

[Structure (c): amide —N(H)—C(=O)—R₅]

-continued (d)

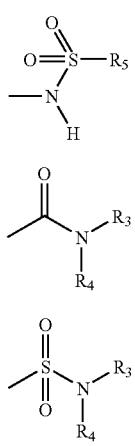

(e)

(f)

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

The present invention further provides novel compounds of the Formula:

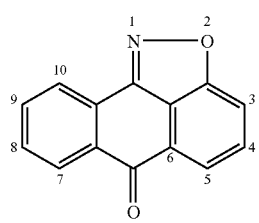

(III)

or pharmaceutically acceptable salts thereof, being (i) monosubstituted and having a first substituent or (ii) disubstituted and having a first substituent and a second substituent;

the first or second substituent, when present, is at the 3, 4, 5, 7, 8, 9, or 10 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c) (d), (e), or (f):

(a)

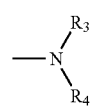

(b)

—N(H)—(alkyl)—N(R₃)(R₄)

(c)

—N(H)—C(=O)—R₅

(d)

—N(H)—S(=O)₂—R₅

(e)

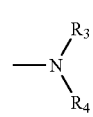

(f)

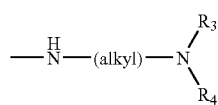

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that if the first substituent is halogen or alkoxy, the compound is disubstituted.

In one embodiment, the first and second substituent of compounds of Formula III, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

(a)

(b)

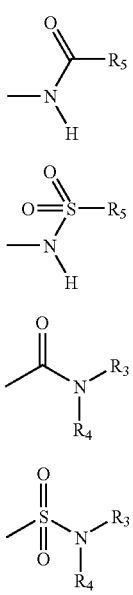

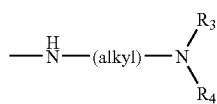

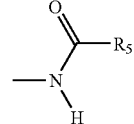

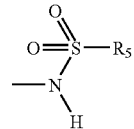

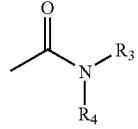

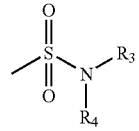

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that if the first substituent is halogen or alkoxy, the compound is disubstituted.

The present invention further provides novel compounds of the Formula:

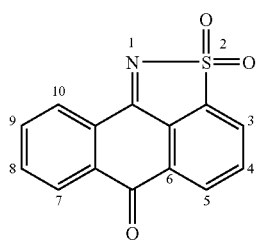

(IV)

or pharmaceutically acceptable salts thereof, being (i) monosubstituted and having a first substituent present at the 5, 7, or 9 position, (ii) disubstituted and having a first substituent present at the 5 position and a second substituent present at the 7 position, (iii) disubstituted and having a first substituent present at the 5 position and a second substituent present at the 9 position, or (iv) disubstituted and having a first substituent present at the 7 position and a second substituent present at the 9 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that when the first substituent is present at the 7 position and is halogen, nitro, or a group represented by the formula (a), the compound is disubstituted.

In one embodiment, the first and second substituent of compounds of Formula IV, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

-continued

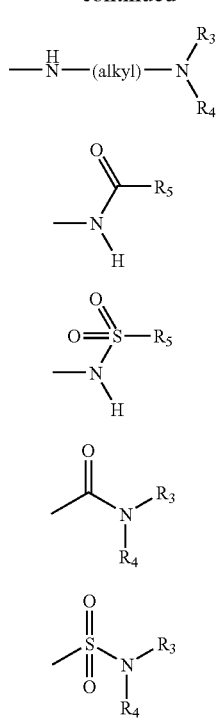

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl;

with the proviso that when the first substituent is present at the 7 position and is halogen, nitro, or a group represented by the formula (a), the compound is disubstituted.

The present invention further provides novel compounds of the Formula:

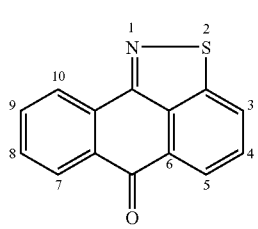

or pharmaceutically acceptable salts thereof, being (i) monosubstituted and having a first substituent present at the 5, 7, or 9 position, (ii) disubstituted and having a first substituent present at the 5 position and a second substituent present at the 9 position, (iii) disubstituted and having a first substituent present at the 7 position and a second substituent present at the 9 position, or (iv) disubstituted and having a first substituent present at the 5 position and a second substituent present at the 7 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

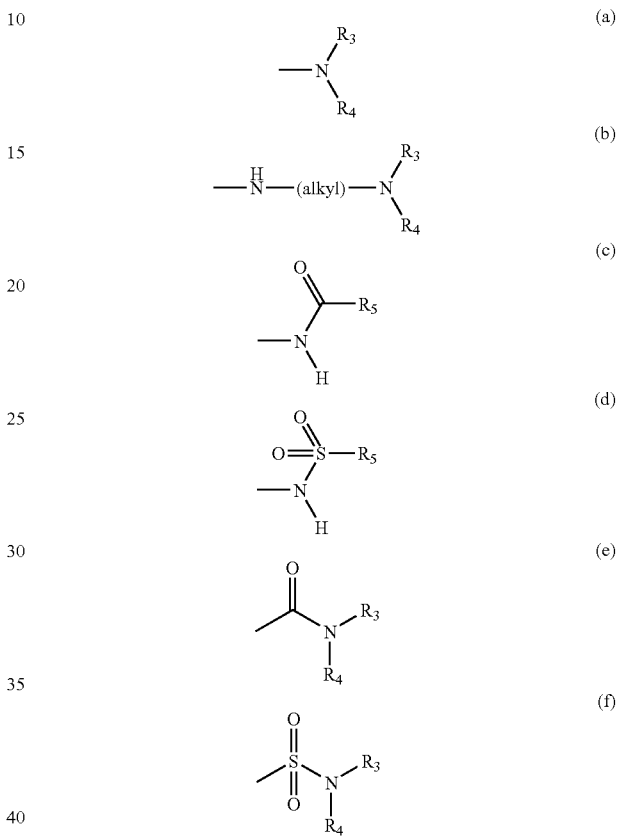

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that if the first substituent is halogen or alkoxy, then the compound is disubstituted;

with the further proviso that if the compound is monosubstituted and has a first substituent at the 5 or 7 position, then the first substituent is a group represented by the formula (e) or (f);

and with the further proviso that if the compound is disubstituted and has a substituent present at the 7 position, then the substituent present at the 7 position is not a group represented by the formula (a) or (c).

In one embodiment, the first and second substituent of compounds of Formula V, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

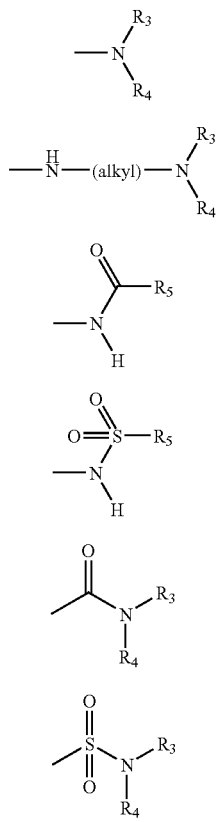

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alky, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl;

with the proviso that if the first substituent is halogen or alkoxy, then the compound is disubstituted;

with the further proviso that if the compound is monosubstituted and has a first substituent at the 5 or 7 position, then the first substituent is a group represented by the formula (e) or (f);

and with the further proviso that if the compound is disubstituted and has a substituent present at the 7 position, then the substituent present at the 7 position is not a group represented by the formula (a) or (c).

The compounds of Formulas (I)-(V), and pharmaceutically acceptable salts thereof, are useful for modulating JNK. Accordingly, the compounds of Formulas (I)-(V), and pharmaceutically acceptable salts thereof, are useful for treating or preventing a disease associated with the modulation of JNK. Preferably, the compounds of Formulas (I)-(V), and pharmaceutically acceptable salts thereof, inhibit JNK. The compounds of Formula (I)-(V), or pharmaceutically acceptable salts thereof, are also useful for treating cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy; myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

The invention also relates to pharmaceutical compositions comprising a compound of Formula (I)-(V), or a pharmaceutically acceptable salt thereof, and a pharmaceutically acceptable carrier or vehicle.

The present invention further relates to pharmaceutical compositions comprising:

(A) a compound having the formula:

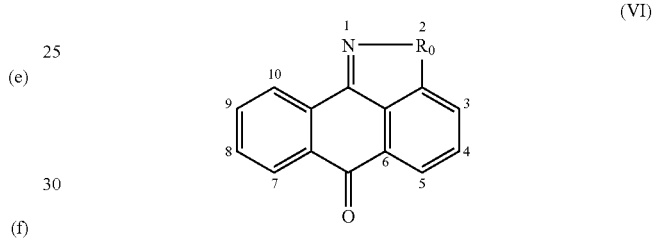

(VI)

or a pharmaceutically acceptable salt thereof, wherein R₀ is —O—, —S—, —S(O)—, —S(O)₂— or —CH₂—;

the compound being (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):.

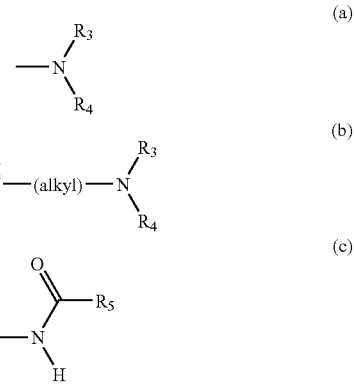

-continued (d)
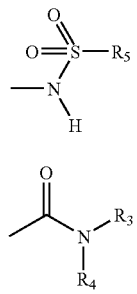

(e)
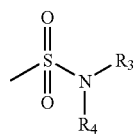

(f)
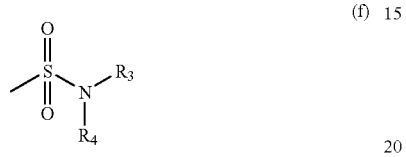

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl; and (B) a pharmaceutically acceptable carrier or vehicle.

In one embodiment, the first or second substituent of compounds of Formula VI, when present, is at the 3, 4, 5, 7, 8, 9, or 10 position, wherein the first and second substituent, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):.

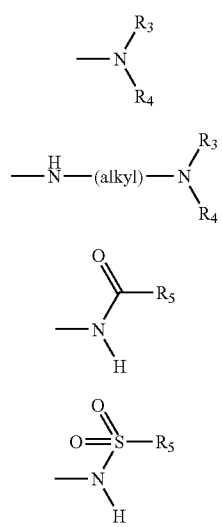

(e)
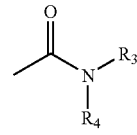

(f)
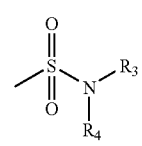

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, monoalkylaminioalkyl, or di-alkylaminoalkyl.

The compositions are useful for modulating JNK. Accordingly, the compositions are useful for treating or preventing a disease associated with the modulation of JNK. Preferably, the compositions inhibit JNK. The compositions are also useful for treating cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy; myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

The invention also relates to methods for treating or preventing a disease associated with modulation of JNK, which comprises administering to a patient in need thereof an effective amount of a compound of the Formula (I)-(VI), or a pharmaceutically acceptable salt thereof.

The invention further relates to a method for treating or preventing a disorder, which comprises administering to a patient in need thereof an effective amount of a compound of the Formula (I)-(VI), or a pharmaceutically acceptable salt thereof, wherein the disorder is cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy, myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

The present invention further relates to a method for treating or preventing cancer, which comprises administering to a patient in need thereof an effective amount of a compound of the Formula (I)-(VI), or a pharmaceutically acceptable salt thereof.

The present invention may be understood more fully by reference to the brief description of the drawings, detailed description, and examples, which are intended to exemplify non-limiting embodiments of the invention.

4. BRIEF DESCRIPTION OF THE DRAWINGS

FIG. 1 describes the effect of Compound CC on dopamine uptake in rat ventral mesencephalan neurons following exposure to the neurotoxin 6-OHDA. In FIG. 1 ♦ represents ventral mesencephalan neurons treated only with 6-OHDA and -♦- represents ventral mesencephalan neurons treated with 6-OHDA and Compound CC.

5. DETAILED DESCRIPTION OF THE INVENTION

5.1 Definitions

As used herein, the terms used above have the following meaning:

"Alkyl" means a straight chain or branched, saturated or unsaturated chain having from 1 to 8 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, and n-hexyl, and longer alkyl groups, such as heptyl, and octyl. An alkyl group can be unsubstituted or substituted. Unsaturated alkyl groups include alkenyl groups and alkynyl groups, discussed below.

An "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to, ($C_2$-$C_6$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted.

An "alkynyl group" means a monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted.

"Halogen" means fluorine, chlorine, bromine, or iodine.

"Trifluoromethyl" means —$CF_3$.

"Sulfonyl" means —$SO_3H$;

"Carboxyl" means —COOH.

"Alkoxy" means —O-(alkyl), wherein alkyl is defined above.

"Alkoxyalkoxy" means —O-(alkyl)-O-(alkyl), wherein each "alkyl" is independently an alkyl group defined above. Preferably, akoxyalkoxy is —$OCH_2OCH_3$ or —$OCH_2CH_2OCH_3$.

"Alkoxycarbonyl" means —C(=O)O-(allyl), wherein alkyl is defined above.

"Alkoxycarbonylalkyl" means -(alkyl)-C(=O)O-(alkyl), wherein alkyl is defined above.

"Alkoxyalkyl" means -(alkyl)-O-(alkyl), wherein each "alkyl" is independently an alkyl group defined above. Preferably, alkoxyalkyl is —$CH_2OCH_3$ or —$CH_2OCH_2CH_3$.

"Aryl" means a carbocyclic or heterocyclic aromatic group containing from 5 to 10 ring atoms. The ring atoms of a carbocyclic aromatic group are all carbon atoms, and include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. A carbocyclic aromatic group can be unsubstituted or substituted. Preferably, the carbocyclic aromatic group is a phenyl group. The ring atoms of a heterocyclic aromatic group contains at least one heteroatom, preferably 1 to 3 heteroatoms, independently selected from nitrogen, oxygen, and sulfur. Illustrative examples of heterocyclic aromatic groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phenyl, isoxazolyl, indolyl, oxetanyl, azepinyl, piperazinyl, morpholinyl, dioxanyl, thietanyl and oxazolyl. A heterocyclic aromatic group can be unsubstituted or substituted. Preferably, a heterocyclic aromatic is a monocyclic ring, wherein the ring comprises 2 to 5 carbon atoms and 1 to 3 heteroatoms.

"Aryloxy" means —O-aryl group, wherein aryl is as defined above. An aryloxy group can be unsubstituted or substituted. Preferably, the aryl ring of an aryloxy group is a phenyl group.

"Arylalkyl" means -(alkyl)-(aryl), wherein alkyl and aryl are defined above. Preferably arylalkyl is benzyl (i.e., —$CH_2$-phenyl) or —$CH_2$-pyrindinyl.

"Arylalkyloxy" means —O-(alkyl)-(aryl), wherein alkyl and aryl are defined above. Preferably, arylalkyloxy is —O-benzyl or —O—$CH_2$-pyridinyl.

"Cycloalkyl" means a monocyclic or polycyclic saturated ring comprising carbon and hydrogen atoms and having no carbon-carbon multiple bonds. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

"Cycloalkyloxy" means —O-(cycloalkyl), wherein cycloalkyl is defined above.

"Cycloalkylalkyloxy" means —O-(alkyl)-(cycloalkyl), wherein cycloalkyl and alkyl are defined above. Preferably, cycloalkylalkyloxy is —$OCH_2$-cyclohexyl.

"Alkylidene" means the divalent radical —$C_nH_{2n}$—, wherein n is an integer from 1 to 8, such as —$CH_2$—, —$CH_2CH_2$—, —$CH_2$—$CH_2$—$CH_2$—, —$CH_2CH_2CH_2CH_2$—, —$CH_2CH_2CH_2CH_2CH_2$—, and the like, unsubstituted or substituted with one or more alkyl groups.

"Heteroatom-containing alkylidene" means an alkylidene wherein at least one carbon atom is replaced by a heteroatom selected from nitrogen, oxygen, or sulfur, such as —$CH_2CH_2OCH_2CH_2$—, and the like, unsubstituted or substituted with one or more alkyl groups.

"Aminoalkoxy" means —O-(alkyl)-$NH_2$, wherein alkyl is defined above.

"Mono-alkylamino" means —NH(alkyl), wherein alkyl is defined above.

"Di-alkylamino" means —N(alkyl)(alkyl), wherein each "alkyl" is independently an alkyl group defined above.

"Mono-alkylaminoalkoxy" means —O-(alkyl)-NH(alkyl), wherein each "alkyl" is independently an alkyl group defined above.

"Di-alkylaminoalkoxy" means —O-(alkyl)N(alkyl)(alkyl), wherein each "alkyl" is independently an alkyl group defined above.

"Arylamino" means —NH(aryl), wherein aryl is defined above.

"Arylalkylamino" means —NH-(alkyl)-(aryl), wherein alkyl and aryl are defined above. Preferably, arylalkylamino is —NH-benzyl or —NHCH$_2$-pyridinyl.

"Alkylamino" means —NH(alkyl), wherein alkyl is defined above.

"Cycloalkylamino" means —NH-(cycloalkyl), wherein cyclohexyl is defined above.

"Cycloalkylalkylamino" means —NH-(alkyl)-(cycloalkyl), wherein alkyl and cloalkyl are defined above. Preferably, cycloalkylalkylamino is —NHCH$_2$-cyclohexyl.

"Aminoalkyl" means -(alkyl)-NH$_2$, wherein alkyl is defined above.

"Mono-alkylaminoalkyl" means -(alkyl)-NH(alkyl), wherein each "alkyl" is independently an allyl group defined above.

"Di-alkylaminoalkyl" means -(alkyl)-N(alkyl)(alkyl), wherein each "alkyl" is independently an alkyl group defined above.

The phrase "modulation of JNK" or "by modulating JNK" means the inhibition or activation, preferably the inhibition, of a protein and all isoforms thereof expressed by JNK 1, JNK 2, and JNK 3 genes.

By "JNK" is meant a protein and all isoforms thereof expressed by JNK 1, JNK 2, and JNK 3 genes.

The phrase "pharmaceutically acceptable salt(s)," as used herein includes, but is not limited to, salts of acidic or basic groups that can be present in compounds of Formula (I)-(VI). Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, trifluoroacetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, and pamoic (i.e., 1,1'-methylene-bis-(2-hydroxy-3-naphthoate) acids. Suitable inorganic acids include hydrochloric, hydrobromic, hydroiodic, sulfuric, phosphoric, and nitric acids. Compounds that include an amine moiety can form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Thus, the term "pharmaceutically acceptable salt(s)" of a compound of Formula (I)-(VI) is intended to encompass any and all acceptable salt forms.

5.2 Novel Compounds 5.2.1 Compounds of Formula (I)

The present invention encompasses novel compounds having the general Formula (I):

and pharmaceutically acceptable salts thereof, being (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

In one embodiment, the first and second substituent of compounds of Formula I, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

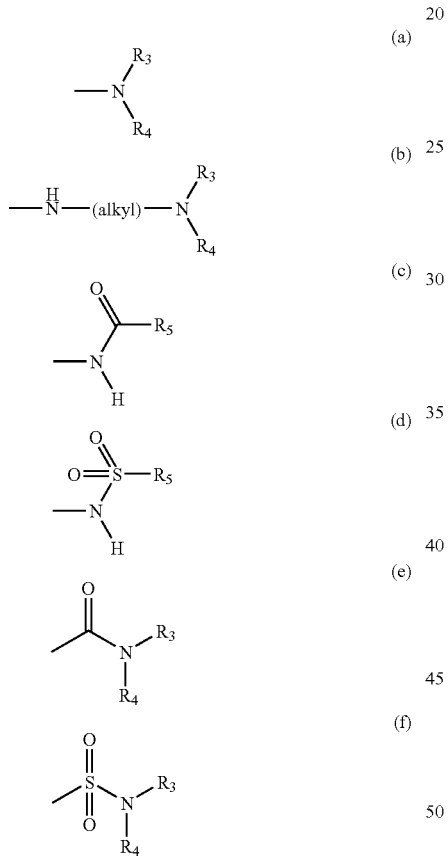

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

A preferred subclass of the compounds of Formula (I) is that wherein the first or second substituent are present at the 5, 7, or 9 position. More preferably, the first or second substituent are present at the 5 or 7 position.

A second preferred class of compounds of formula (I) is that wherein:

the first or second substituent are present at the 5, 7, or 9 position;

the first or second substituent are independently alkoxy, aryloxy, aminoalkyl, mono-alkylaminoalkyl, di-alkylaminoalkyl, or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, or cycloalkylalkyl.

5.2.2 Compounds of Formula (II)

The present invention encompasses novel compounds having the general Formula (II):

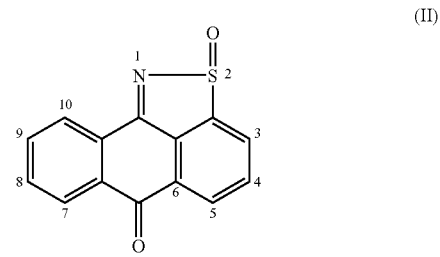

and pharmaceutically acceptable salts thereof, being (i) unsubstituted, (ii) monosubstituted and having a first substituent, or (ii) disubstituted and having a first substituent and a second substituent;

the first or second substituent, when present, is at the 3, 4, 5, 7, 8, 9, or 10 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b) (c), (d), (e), or (f):

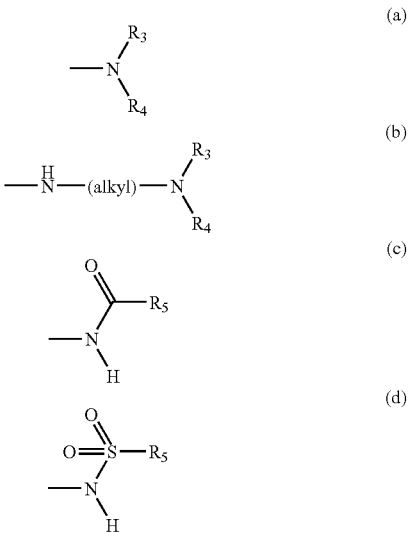

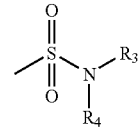

(e)

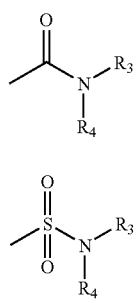

(f)

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

In one embodiment, the first and second substituent of compounds of Formula II, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b) (c), (d), (e), or (f):

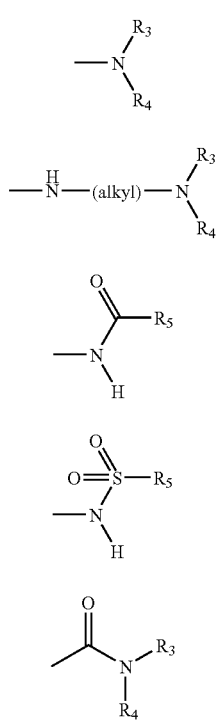

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

A preferred subclass of the compounds of Formula (II) is that wherein the first or second substituent are present at the 5, 7, or 9 position. More preferably, the first or second substituent are present at the 5 or 7 position.

A second preferred subclass of the compounds of Formula (II) is that wherein:

the first or second substituent are independently alkoxy, aryloxy, or a group represented by the formula (a), (c), (d), (e), or (f);

R₃ and R₄ are independently hydrogen, alkyl, cycloalkyl, aryl, arylalkyl, or cycloalkylalkyl; and R₅ is hydrogen, alkyl, cycloalkyl, aryl, arylalkyl, or cycloalkylalkyl.

5.2.3 Compounds of Formula (III)

The present invention encompasses novel compounds having the general Formula (III):

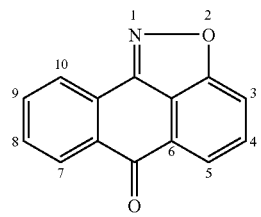

(III)

and pharmaceutically acceptable salts thereof, being (i) monosubstituted and having a first substituent or (ii) disubstituted and having a first substituent and a second substituent;

the first or second substituent, when present, is at the 3, 4, 5, 7, 8, 9, or 10 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c) (d), (e), or (f):

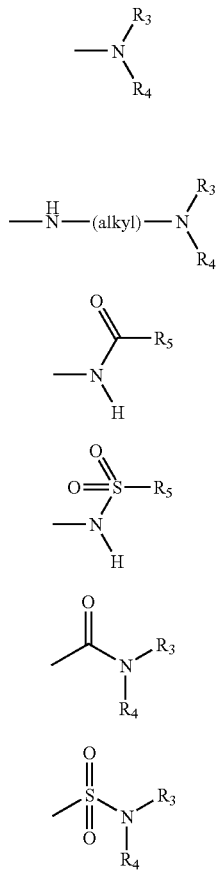

(a), (b), (c), (d), (e), (f)

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that if the first substituent is halogen or alkoxy, the compound is disubstituted.

In one embodiment, the first and second substituent of compounds of Formula III, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c) (d), (e), or (f):

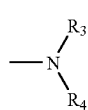

(a)

-continued

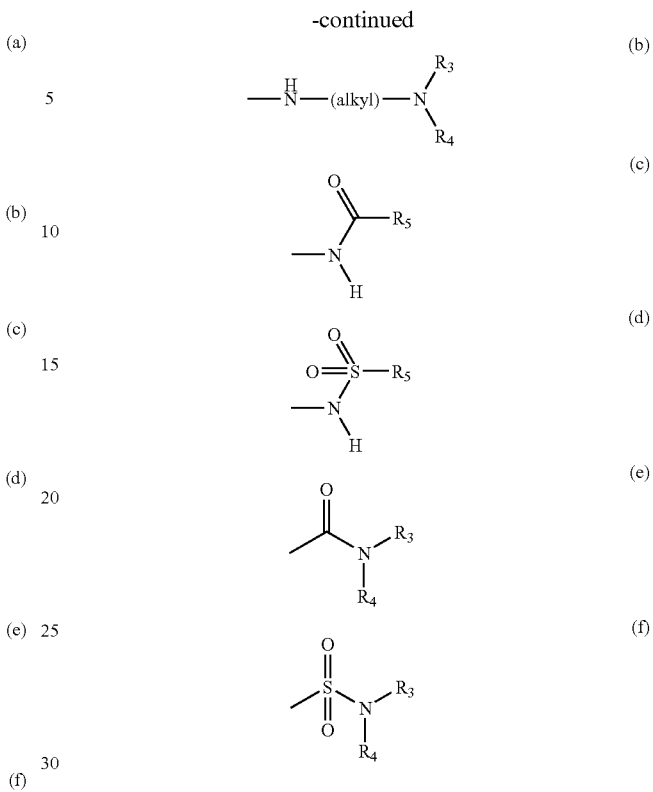

(b), (c), (d), (e), (f)

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that if the first substituent is halogen or alkoxy, the compound is disubstituted.

A preferred subclass of the compounds of Formula (III) is that wherein the first or second substituent are present at the 5, 7, or 9 position. More preferably, the first or second substituent are present at the 5 or 7 position.

A second preferred subclass of the compounds of Formula (m) is that wherein:

the first or second substituent are independently alkoxy, aryloxy, aminoalkyl, mono-alkylaminoalkyl, di-alkylaminoalkyl, or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, or cycloalkylalkyl.

5.2.4 Compounds of Formula (IV)

The present invention encompasses novel compounds having the general Formula (IV):

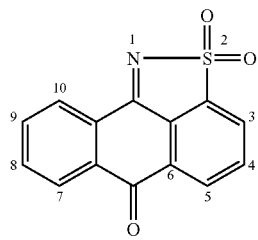

(IV)

and pharmaceutically acceptable salts thereof, being (i) monosubstituted and having a first substituent present at the 5, 7, or 9 position, (ii) disubstituted and having a first substituent present at the 5 position and a second substituent present at the 7 position, (iii) disubstituted and having a first substituent present at the 5 position and a second substituent present at the 9 position, or (iv) disubstituted and having a first substituent present at the 7 position and a second substituent present at the 9 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

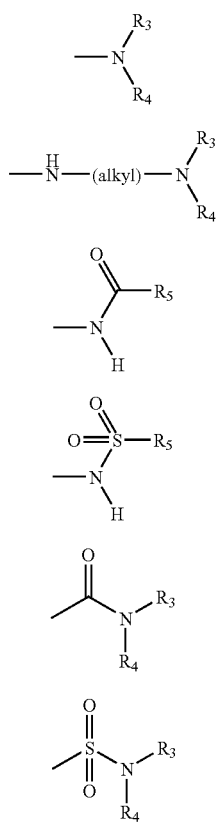

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that when the first substituent is present at the 7 position and is halogen, nitro, or a group represented by the formula (a), the compound is disubstituted.

In one embodiment, the first and second substituent of compounds of Formula IV, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

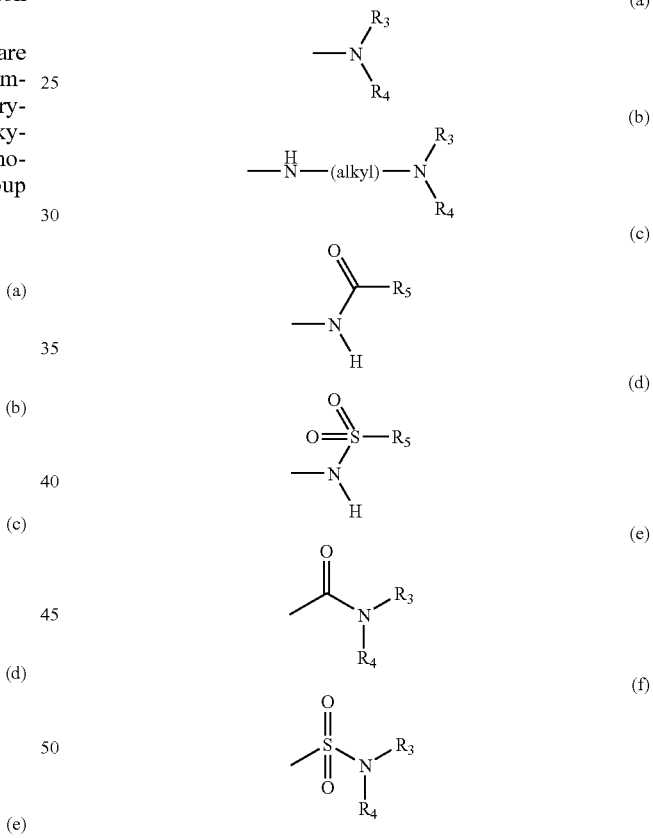

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that when the first substituent is present at the 7 position and is halogen, nitro, or a group represented by the formula (a), the compound is disubstituted.

A preferred class of the compounds of Formula (V) is that wherein the first or second substituent are present at the 5 or 7 position.

A second preferred subclass of the compounds of Formula (IV) is that wherein the first or second substituent are independently alkyl, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (c), (d), (e), or (f).

Another preferred subclass of the compounds of Formula (IV) is that wherein:

the first and second substituent are independently alkoxy, aryloxy, or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonyl, or cycloalkylalkyl.

5.2.5 Compounds of Formula (V)

The present invention encompasses novel compounds having the general Formula (V):

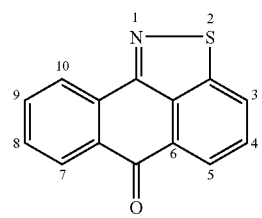

(V)

and pharmaceutically acceptable salts thereof, being (i) monosubstituted and having a first substituent present at the 5, 7, or 9 position, (ii) disubstituted and having a first substituent present at the 5 position and a second substituent present at the 9 position, (iii) disubstituted and having a first substituent present at the 7 position and a second substituent present at the 9 position, or (iv) disubstituted and having a first substituent present at the 5 position and a second substituent present at the 7 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

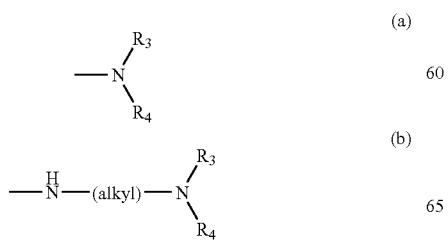

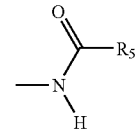

(c)

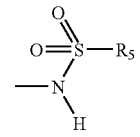

(d)

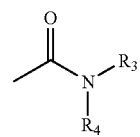

(e)

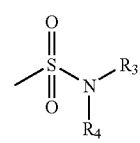

(f)

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

with the proviso that if the first substituent is halogen or alkoxy, then the compound is disubstituted;

with the further proviso that if the compound is monosubstituted and has a first substituent at the 5 or 7 position, then the first substituent is a group represented by the formula (e) or (f);

and with the further proviso that if the compound is disubstituted and has a substituent present at the 7 position, then the substituent present at the 7 position is not a group represented by the formula (a) or (c).

In one embodiment, the first and second substituent of compounds of Formula V, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

-continued

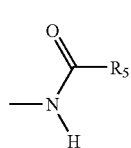
(c)

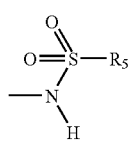
(d)

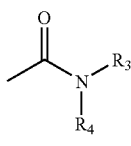
(e)

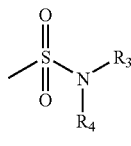
(f)

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, monoalkylaminioalkyl, or di-alkylaminoalkyl;

with the proviso that if the first substituent is halogen or alkoxy, then the compound is disubstituted;

with the further proviso that if the compound is monosubstituted and has a first substituent at the 5 or 7 position, then the first substituent is a group represented by the formula (e) or (f);

and with the further proviso that if the compound is disubstituted and has a substituent present at the 7 position, then the substituent present at the 7 position is not a group represented by the formula (a) or (c).

A preferred subclass of the compounds of Formula (V) is that wherein the first or second substituent are present at the 5 or 7 position.

A second preferred subclass of the compounds of Formula (V) is that wherein the compound of Formula (V) is disubstituted and at least one of the substituents is a group represented by the formula (d) or (f).

Another preferred class of the compounds of Formula (V) is that wherein the compounds are monosubstituted. Most preferred are compounds that are monosubstituted at the 5 or 7 position with a group represented by the formula (e) or (f).

The compounds of Formulas (I)-(V), and pharmaceutically acceptable salts thereof, are useful for modulating JNK. Accordingly, the compounds of Formulas (I)-(V), and pharmaceutically acceptable salts thereof, are useful for treating or preventing a disease associated with the modulation of JNK. Preferably, the compounds of Formulas (I)-(V), and pharmaceutically acceptable salts thereof, inhibit JNK. The compounds of Formula (I)-(V), or pharmaceutically acceptable salts thereof, are also useful for treating cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy; myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

5.3 Synthesis 5.3.1 Synthesis of the Compounds of Formula (I)

Compounds of Formula (I), the compound of Formula (I) being defined above, can be prepared in a two step procedure depicted in Reaction Scheme 1 below.

Reaction Scheme 1

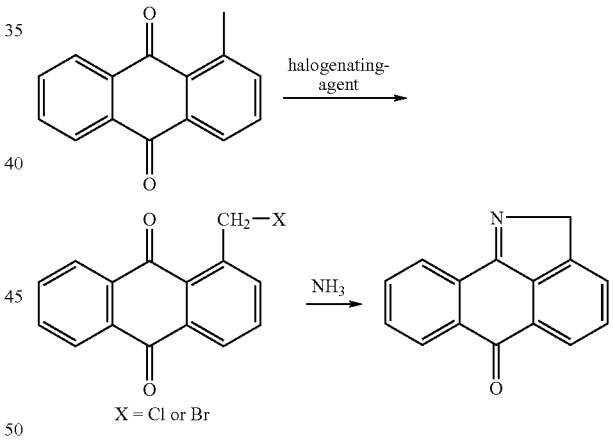

X = Cl or Br

The first step involves halogenation of 1-methylanthraquinone or an appropriately monosubstituted or disubstituted 1-methylanthroquinone with a halogenating agent in a suitable solvent, or in the absence of solvent, at temperatures from about 25° C. to about 200° C. for about 1 to about 16 hours. Representative halogenating agents include, but are not limited to, thionyl chloride, thionyl bromide, $POCl_3$, $POBr_3$, N-bromosuccinimide, and N-chlorosuccinimide. Suitable solvents are, for example, benzene, tetrahydrofuran (THF), and ether. The resulting halogenated intermediate is then treated with ammonia in a suitable solvent at temperatures from about 25° C. to about 200° C. for about 1 to about 16 hours. Suitable solvents are, for example, ethanol and methanol.

The compounds of Formula (I) can also be prepared by the two step procedure depicted in Reaction Scheme 2 below.

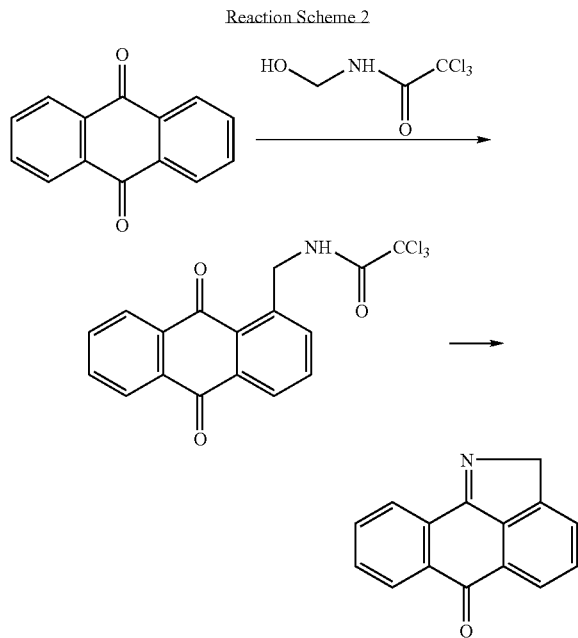

The first step involves reacting anthroquinone or an appropriately monosubstituted or disubstituted anthroquinone with trichloroacetic acid-(hydroxymethyl-amide) in the presence of an acid, such as sulfuric acid or hydrochloric acid, in a suitable solvent or in the absence of solvent, to provide a 2,2,2-trichloroacetyl-aminomethyl substituted anthraquinone. Suitable solvents are, for example, nitrobenzene, dichlorobenzene, and nitromethane. The second step involves reacting the 2,2,2-trichloroacetyl-aminomethyl substituted anthraquinone with a base catalyst in a suitable solvent. Suitable base catalysts include, but are not limited to, sodium hydroxide, potassium hydroxide, potassium carbonate, sodium methoxide, and sodium ethoxide. Suitable solvents are, for example, water, methanol, and ethanol.

5.3.2 Synthesis of the Compounds of Formula (II)

Compounds of Formula (II), the compound of Formula (II) being defined above, can be prepared by oxidizing compounds of Formula (V) with a stoichiometric amount of a mild oxidizing agent in a suitable solvent at temperatures from about 0° C. to about 200° C. for about 1 to about 24 hours. Suitable reducing agents include, but are not limited to, sodium hypochlorite, meta-chloroperbenzoic acid, pyridinium chlorochromate, dipyridine Cr(VI) oxide, and pyridinium dichromate. Suitable solvents are, for example, hydrocarbon solvents and chlorinated solvents, such as methylene chloride and carbon tetrachloride.

5.3.3 Synthesis of the Compounds of Formula (III)

Compounds of Formula (III), the compound of Formula (III) being defined above, can be prepared by condensing anthroquinone or an appropriately monosubstituted or disubstituted anthroquinone, having a leaving group, X, at the 1 position, with hydroxylamine as depicted in Reactions Scheme 3 below.

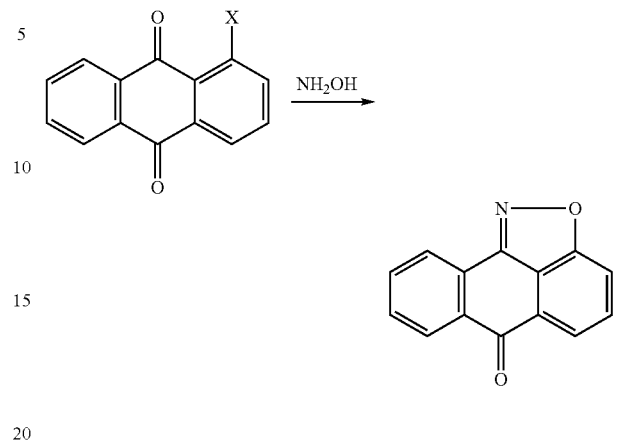

The reaction is carried out in a suitable solvent at temperatures from about 0° C. to about 200° C. for about 1 to about 16 hours. Suitable solvents are, for example, ethanol, methanol, and THF. Suitable leaving groups include, but are not limited to fluoro, chloro, bromo, iodo, nitro, methanesulfonyloxy, tosyloxy, and phenoxy.

5.3.4 Synthesis of the Compounds of Formula (IV)

Compounds of Formula (IV), the compound of Formula (IV) being defined above, can be prepared by oxidizing compounds of Formula (V) with an excess of the oxidizing agents used to prepare the compounds of Formula (II). The reaction is conducted in a suitable solvent at temperatures from about 0° C. to about 200° C. for about 1 to about 24 hours. Suitable solvents are, for example, hydrocarbon solvents and chlorinated solvents, such as methylene chloride, and carbon tetrachloride.

Compounds of Formula (IV) can also be prepared by oxidation of the compounds of Formula (V) with $CrO_3$ in a suitable solvent at temperatures from about 0° to about 100° C. for about 1 to about 16 hours, as depicted in Reaction Scheme 4 below.

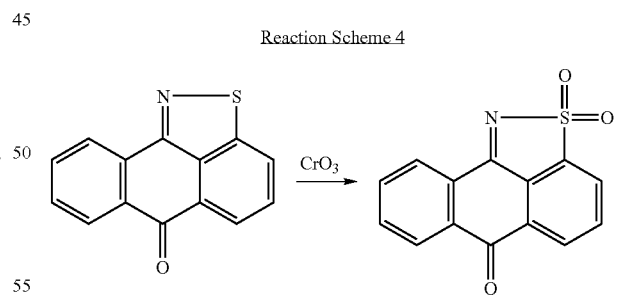

Suitable solvents are, for example, acetic acid, formic acid, an aqueous HCl.

5.3.5 Synthesis of the Compounds of Formula (V)

Compounds of Formula (V), the compound of Formula (V) being defined above, can be prepared by condensing anthroquinone or an appropriately monosubstituted or disubstituted anthroquinone with ammonium thiocyanate, as depicted in Reaction Scheme 5 below.

Reaction Scheme 5

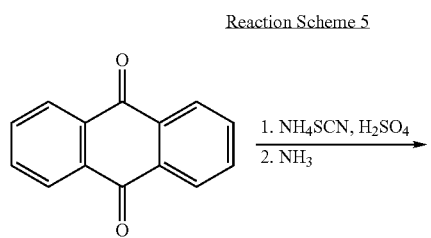

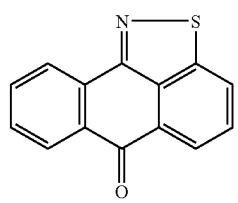

The reaction is carried out in a suitable solvent at temperatures from about 0° C. to about 200° C. for about 1 to about 24 hours. Suitable solvents are, for example, pyridine, dimethylformamide, dimethylsulfoxide (DMSO), and dioxane The resulting intermediate is then reacted with ammonia in a suitable solvent, or in the absence of solvent, at temperatures from about 25° C. to about 200° C. for about 1 to about 24 hours. Suitable solvents are, for example, ethanol, methanol, and water.

The compounds of Formula (V) can also be prepared by a two step procedure depicted in Reaction Scheme 6 below.

Reaction Scheme 6

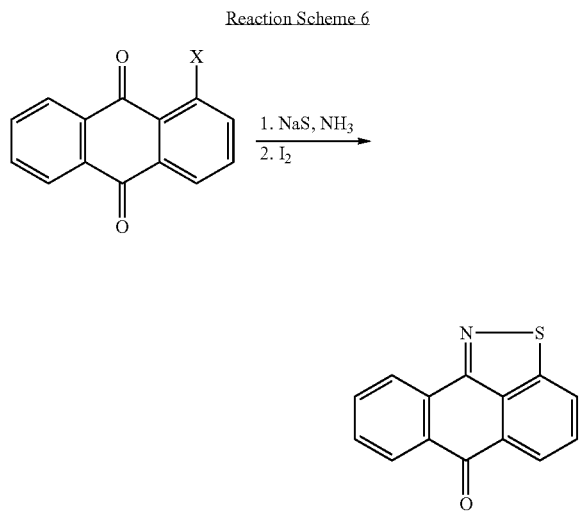

The first step involves condensing an appropriately substituted anthroquinone having a leaving group, X, at the 1-position, with sodium sulfide in the presence of ammonia in a suitable solvent. Representative leaving groups include, but are not limited to fluoro, chloro, bromo, iodo, nitro, methanesulfonyloxy, tosyloxy, and phenoxy. Suitable solvents are, for example, pyridine, dimethylformamide, methylene chloride, chloroform, ethanol, and dioxane. The reaction is carried out at temperatures from about 0° C. to about 200° C. for about 1 to about 16 hours. The resulting intermediate is then treated with iodine and a base, such as, but not limited to, sodium acetate, sodium phosphate, or sodium bicarbonate in a suitable solvent. Suitable solvents are, for example, benzene, toluene, nitrobenzene, dichlorobenzene, and xylenes. The reaction is carried out at temperatures from about 0° C. to about 200° C. for about 1 to about 16 hours.

5.3.6 Synthesis of the Compounds of Formula (VI)

Compounds of Formula (VI), the compound of Formula (VI) being defined above, with 5-amino substituents can be prepared by condensing an appropriately substituted compound of Formula (VI), having a leaving group, X, at the 5 position, with ammonia, a mono-substituted amine, or a di-substituted amine at temperatures from about 0° C. to about 250° C. for about 1 to about 16 hours, either in a suitable solvent or the absence of a solvent as depicted in Reaction Scheme 7 below.

Reaction Scheme 7

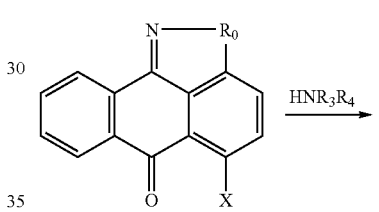

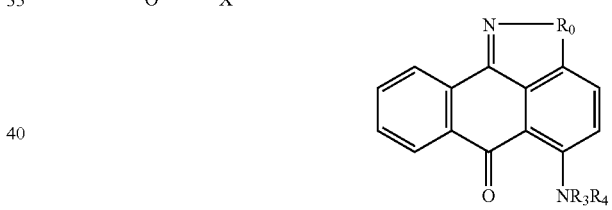

Representative leaving groups include, but are not limited to chloride, bromide, iodide, methanesulfonate, tosyl, benzenesulfonate, and triflate. Suitable solvents are, for example, pyridine, dimethylformamide, dimethylsulfoxide, dichloroethane, chloroform, tetrahydrofuran, dioxane, diglyme, and triglyme. The reaction is conducted in the presence of an excess amount of the amine, or in the presence of an acid quenching agent such as triethylamine, diisopropylethylamine, sodium bicarbonate, potassium carbonate, or sodium hydroxide.

The compound of Formula (VI), having a leaving group, X, at the 5 position, wherein X is chloro can be prepared, for example, by condensing 1,4-dichloroanthroquinone with ammonium thiocyanate using the method described in Reaction Scheme 5.

Compounds of Formula (VI) with 5-amino substituents can also be prepared by condensing an appropriately substituted compound of Formula (VI) with an amino group at the 5-position with an alkyl group containing a good leaving group, X, ($R_3X$) at temperatures from about 25° C. to about 250° C. for about 1 to about 24 hours, in a suitable solvent or in the absence of solvent as depicted in Reaction Scheme 8 below.

Reaction Scheme 8

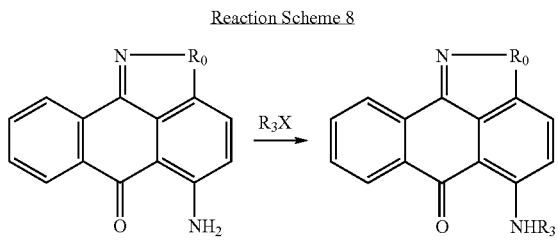

Representative leaving groups include, but are not limited to, chloride, bromide, iodide, methanesulfonate, tosylate, benzenesulfonate, and triflate. Suitable solvents are, for example, pyridine, dimethylformamide, dimethylsulfoxide, dichloroethane, chloroform, tetrahydrofuran, dioxane, diglyme, and triglyme. The reaction is conducted in the presence of an excess amount of the amine, or in the presence of an acid quenching agent such as triethylamine, diisopropylethylamine, sodium bicarbonate, potassium carbonate, or sodium hydroxide.

Similarly, compounds of Formula (VI) with 7-amino substituents can be prepared by condensing an appropriately substituted compound of Formula (VI), having a leaving group, X, at the 7 position, with ammonia, a mono-substituted amine, or a di-substituted amine at temperatures from about 0° C. to about 250° C. for about 1 to about 16 hours, either in a suitable solvent or the absence of a solvent as depicted in Reaction Scheme 9 below.

Reaction Scheme 9

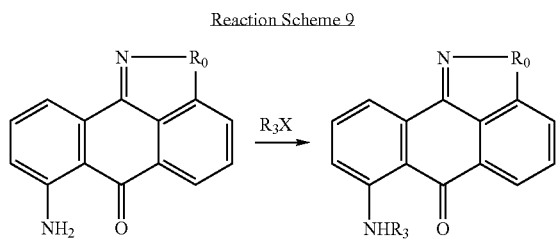

Representative leaving groups include, but are not limited to, chloride, bromide, iodide, methanesulfonate, tosylate, benzenesulfonate, and triflate. Suitable solvents are, for example, pyridine, dimethylformamide, dimethylsulfoxide, dichloroethane, chloroform, tetrahydrofuran, dioxane, diglyme, and triglyme. The reaction is conducted in the presence of an excess amount of the amine, or in the presence of an acid quenching agent such as triethylamine, diisopropylethylamine, sodium bicarbonate, potassium carbonate, or sodium hydroxide.

Compounds of Formula (VI) with 7-amino substituents can also be prepared by condensing an appropriately substituted compound of Formula (VI) with an amino group at the 7-position with an alkyl group containing a good leaving group, X, ($R_3X$) at temperatures of from about 25° C. to about 250° C. for about 1 to about 24 hours, in a suitable solvent or in the absence of solvent as depicted in Reaction Scheme 10 below.

Reaction Scheme 10

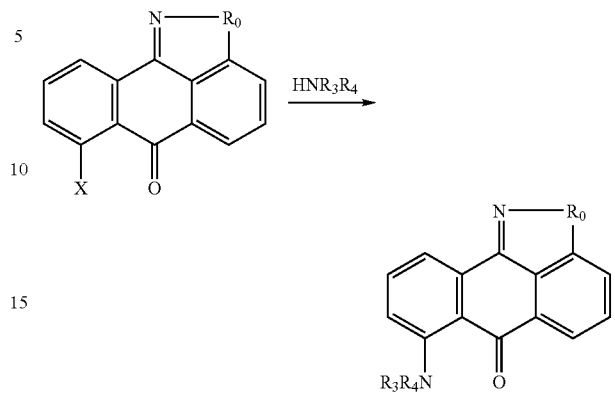

Representative leaving groups include, but are not limited to, chloride, bromide, iodide, methanesulfonate, tosylate, benzenesulfonate, and triflate. Suitable solvents are, for example, pyridine, dimethylformamide, dimethylsulfoxide, dichloroethane, chloroform, tetrahydrofuran, dioxane, diglyme, and triglyme. The reaction is conducted in the presence of an excess amount of the amine, or in the presence of an acid quenching agent such as triethylamine, diisopropylethylamine, sodium bicarbonate, potassium carbonate, or sodium hydroxide.

Similarly, amine substituents at other positions on the aromatic ring can be converted to substituted amines at their respective positions. Anthroquinones substituted with amine at other positions are known (Kopetschni, Wiesler Monatsh. Chem (1922), 43, 84; Shah et al., Indian Journal of Chemistry (1976), 14B, 625; Ayyangar, N., Lahoti, R. J., Wagle, D. R. Indian Journal of Chemistry (1978), 16B, 1007).

Compounds of Formula (VI) with 5-carboxyamide substituents can be prepared by condensing an appropriately substituted compound of Formula (VI), having a carboxylic acid group at the 5 position, with ammonia, a mono-substituted amine, or a di-substituted amine at temeratures from about 0° C. to about 100° C. for about 1 to about 16 hours using a coupling agent in a suitable solvent as depicted in Reaction Scheme 11 below.

Reaction Scheme 11

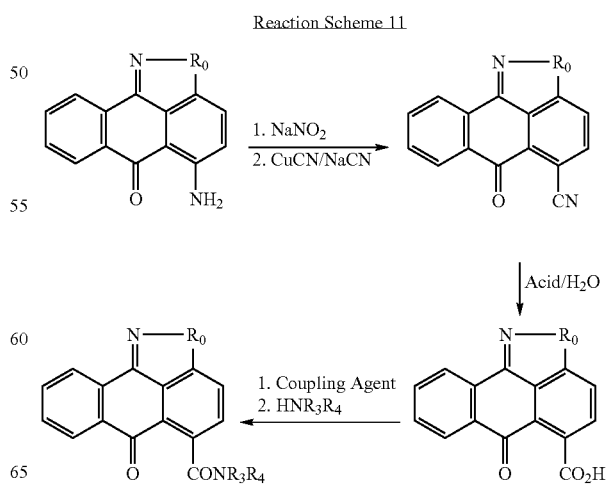

Representative coupling agents include, but are not limited to dicyclohexylcarbodiimide (DCC), 1-(3-dimethylaminopropyl)-3-ethylcarbodiimide hydrochloride (EDCI), and O-(7-azabenzotriazol-1-yl)-N,N,N',N'-tetramethyluronium-hexafluorophosphate (HATU). Suitable solvents are, for example, methylene chloride, chloroform, toluene, dimethylformamide, and tetrahydrofuran.

The starting carboxylic acid may be prepared from a compound of Formula (VI) substituted at the 5 position with an amino group. The 5-amino group is converted to a nitrile with sodium nitrite in a suitable solvent, such as water, methanol, tetrahydrofuran, or ethanol and an acid such as hydrochloric acid or sulfuric acid at temperatures from about 0° C. to about 100° C. for about 1 to about 10 hours followed by treatment with copper cyanide/sodium cyanide in a suitable solvent such as water, methanol, ethanol, ethyl acetate, or tetrahydrofuran at temperatures from about 0° C. to about 100° C. for about 1 to about 10 hours. The nitrile can then be hydrolyzed with an acid such as acetic acid, formic acid, hydrochloric acid, or sulfuric acid at a temperature from about 25° C. to about 100° C. for about 1 to about 24 hours to provide the carboxylic acid. In a similar manner, carboxylic acid groups at other positions on the aromatic ring can be converted to carboxamide substituents at their respective positions. Carboxylic acid groups at other positions on the aromatic ring can be obtained from compounds of Formula (VI) having amines at other positions on the aromatic ring, as discussed above.

Compounds of Formula (VI) with 5-acylamino or 5-sulfonylamino substituents can be prepared by condensing an appropriately substituted compound of Formula (VI), having an amino group at the 5-position with an acid chloride, $R_5COCl$, or sulfonyl chloride $R_5SO_2Cl$, in a suitable solvent at temperatures from about −20° C. to about 50° C. for about 0.5 to about 16 hours as depicted in Reaction Scheme 12 below.

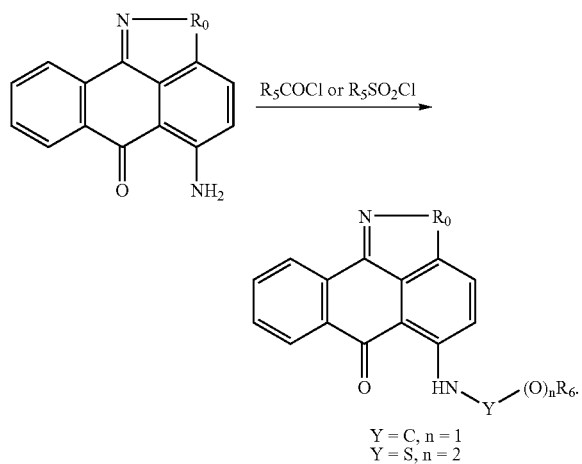

Similarly, compounds of Formula (VI) with 7-acylamino or 7-sulfonylamino substituents can be prepared by condensing an appropriately substituted compound of Formula (VI), having an amino group at the 7-position with an acid chloride, $R_5COCl$, or sulfonyl chloride $R_5SO_2Cl$, in a suitable solvent at temperatures from about −20° C. to about 50° C. for about 0.5 to about 16 hours as depicted in Reaction Scheme 13 below.

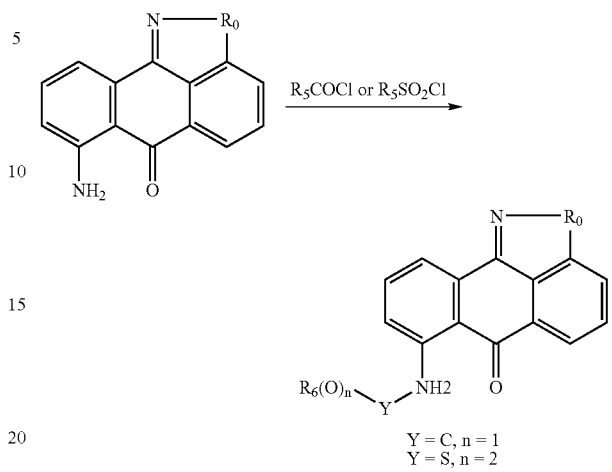

Suitable solvents are, for example, methylene chloride, chloroform, tetrahydrofuran, dioxane, pyridine, dimethylformamide, and ethyl acetate. The reaction is conducted in the presence of an acid quenching agent such as triethylamine, diisopropylethylamine, sodium bicarbonate, potassium carbonate, or sodium hydroxide.

Acylamino or sulfonylamino substituents groups at other positions on the aromatic ring can be obtained from compounds of Formula (VI) having amines at other positions on the aromatic ring, as discussed above.

Compounds of Formula (VI) with 5-alkoxy substituents can be prepared by condensing an appropriately substituted compound of Formula (VI), having a hydroxy group at the 5-position with an alkyl group having a leaving group, X, ($R_6X$) in a suitable solvent at temperatures from about −20° C. to about 100° C. for about 0.5 to about 16 hours as depicted in Reaction-Scheme 14 below.

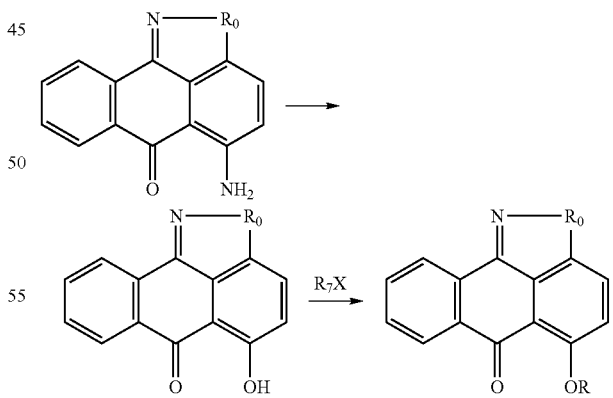

Similarly, compounds of Formula (VI) with 7-alkoxy substituents can be prepared by condensing an appropriately substituted compound of Formula (VI) having a hydroxy group at the 7-position with an alkyl group having a leaving group, X, ($R_6X$) in a suitable solvent at temperatures from about −20° C. to about 100° C. for about 0.5 to about 16 hours as depicted in Reaction Scheme 15 below.

Reaction Scheme 15

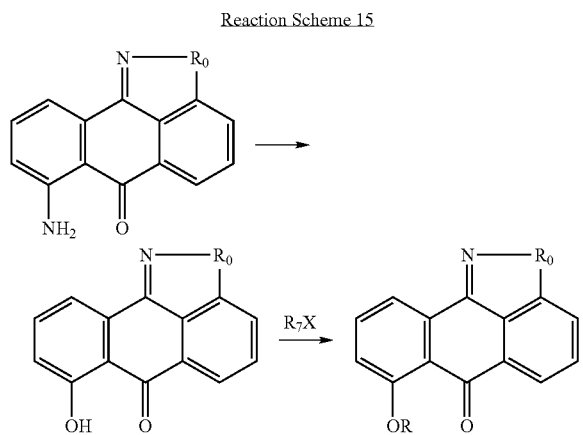

Representative leaving groups, X, include, but are not limited to, chloride, bromide, iodide, methanesulfonate, tosylate, benzenesulfonate, and triflate. Suitable solvents are, for example, methylene chloride, chloroform, tetrahydrofuran, dioxane, dimethylformamide, or ethyl acetate.

The reaction is conducted in the presence of an acid quenching agent such as sodium hydride, triethylamine, diisopropylethylamine, sodium bicarbonate, potassium carbonate, or sodium hydroxide.

The 5-hydroxyanthroquinones and 7-hydroxyanthroquinones can be prepared from the appropriately substituted 5-aminoanthroquinone and appropriately substituted 7-aminoanthroquinone, respectively. The appropriately substituted 5-aminoanthroquinone or appropriately substituted 7-aminoanthroquinone is converted to the alcohol with sodium nitrite in a suitable solvent, such as water, methanol, tetrahydrofuran, or ethanol, and an acid, such as hydrochloric acid or sulfuric acid, at temperatures from about 0° to about 100° C. for about 1 to about 10 hours followed by treatment with an acid, such as hydrochloric acid, sulfuric acid, or phosphoric acid, in water at temperatures from about 0° C. to about 100° C. for about 1 to about 10 hours.

Alternately, the appropriately substituted 5-aminoanthroquinone or appropriately substituted 7-aminoanthroquinone can be heated at temperatures from about 100° C. to about 250° C. in water for about 1 to about 24 hours to provide the compound of Formula (VI) with a hydroxy group at the 5-position or 7-position, respectively. Hydroxyl groups at other positions on the aromatic ring can be obtained from compounds of Formula (VI) having amines at other positions on the aromatic ring, as discussed above.

Disubstituted compounds of Formula (I)-(VI) can be obtained according to one or more of the reaction schemes above. Suitable anthraquinone starting materials that are appropriately substituted are commercially available from a variety of sources or may be prepared by methods well known to those of ordinary skill in the art (See, e.g., Gallagher, P., Contemp. Org. Synth. (1996), 3(5), 433-446; Krohn, K., Tetrahedron (1990), 46(2), 291-318; Vymetal, J., Chem. Listy (1982), 76(8), 846-68; Matsuoka, M., Yuki Gosei Kagaku Kyokaishi (1982), 40(2); Matsuura, A., Nikkakyo Geppo (1978), 31(12); Chung, R. Kirk-Othmer Encycl. Chem. Technol., 3rd Ed., Editors: Grayson, M. and Eckloth, D., Wiley, New York, N.Y., (1978), 2, 708-57; and Chung, R. Kirk-Othmer Encycl. Chem. Technol., 3rd Ed., Editors: Grayson, M. and Eckroth, D., Wiley, New York, N.Y. (1978), 2, 700-7).

5.4 Pharmaceutical Compositions

5.4.1 Pharmaceutical Compositions Comprising a Compound of Formula (I)

The present invention encompasses compositions comprising a compound of Formula (I), the compound of Formula (I) being defined above, or a pharmaceutically acceptable salt thereof, and a pharmaceutically acceptable carrier or vehicle.

In one embodiment, the compound of Formula (I), or a pharmaceutically acceptable salt thereof, is that wherein the first or second substituent is present at the 5, 7, or 9 position. Preferably, the first or second substituent is present at the 5 or 7 position.

In another embodiment, the compound of Formula (I), or a pharmaceutically acceptable salt thereof, is that wherein:
the first or second substituent is present at the 5, 7, or 9 position;
the first and second substituent are independently alkoxy, aryloxy, hydroxy or a group represented by the formula (a), (c), (d), (e), or (f);
$R_3$ and $R_4$ are independently hydrogen, alkyl, cycloalkyl, aryl, arylalkyl, or cycloalkylalkyl; and
$R_5$ is hydrogen, alkyl, cycloalkyl, alkoxycarbonylalkyl, aryl, arylalkyl, or cycloalkylalkyl.

In another embodiment, the compound of Formula (I), or a pharmaceutically acceptable salt thereof, is that wherein:
the first or second substituent is present at the 5, 7, or 9 position;
the first and second substituent are independently alkoxy, aryloxy or a group represented by the formula (a), (c), (d), (e), or (f);
$R_3$ and $R_4$ are independently hydrogen, alkyl, cycloalkyl, aryl, arylalkyl, or cycloalkylalkyl; and
$R_5$ is hydrogen, alkyl, cycloalkyl, aryl, arylalkyl or cycloalkylalkyl.

5.4.2 Pharmaceutical Compositions Comprising a Compound of Formula (II)

The present invention also encompasses compositions comprising a compound of Formula (II), the compound of Formula (II) being defined above, or a pharmaceutically acceptable salt thereof, and a pharmaceutically acceptable carrier or vehicle.

In one embodiment, the compound of Formula (II), or a pharmaceutically acceptable salt thereof, is that wherein the first or second substituent is present at the 5, 7, or 9 position. Preferably, the first or second substituent is present at the 5 or 7 position.

In another embodiment, the compound of Formula (II), or a pharmaceutically acceptable salt thereof, is that wherein:
the first and second substituent are independently alkoxy, aryloxy, hydroxy or a group represented by the formula (a), (c), (d), (e), or (f);
$R_3$ and $R_4$ are hydrogen, alkyl, cycloalkyl, aryl, arylalkyl, or cycloalkylalkyl; and
$R_5$ is hydrogen, alkyl, cycloalkyl, alkoxycarbonylalkyl, aryl, arylalkyl, or cycloalkylalkyl.

In another embodiment, the compound of Formula (II), or a pharmaceutically acceptable salt thereof, is that wherein:
the first and second substituent are independently alkoxy, aryloxy or a group represented by the formula (a), (c), (d), (e), or (f);
$R_3$ and $R_4$ are hydrogen, alkyl, cycloalkyl, aryl, arylalkyl, or cycloalkylalkyl; and R$_5$ is hydrogen, alkyl, cycloalkyl, aryl, arylalkyl or cycloalkylalkyl.

5.4.3 Pharmaceutical Compositions Comprising a Compound of Formula (III)

The present invention also encompasses compositions comprising a compound of Formula (III), the compound of Formula (III) being defined above, or a pharmaceutically acceptable salt thereof, and a pharmaceutically acceptable carrier or vehicle.

In one embodiment, the compound of Formula (III), or a pharmaceutically acceptable salt thereof, is that wherein the first or second substituent is present at the 5, 7, or 9 position. Preferably, the first or second substituent is present at the 5 or 7 position.

In another embodiment, the compound of Formula (III), or a pharmaceutically acceptable salt thereof, is that wherein:

the first and second substituent are independently alkoxy, aryloxy, hydroxy or a group represented by the formula (a), (c), (d), (e), or (f);

R$_3$ and R$_4$ are hydrogen, alkyl, cycloalkyl, aryl, arylalkyl, or cycloalkylalkyl; and R$_5$ is hydrogen, alkyl, cycloalkyl, alkoxycarbonylalkyl, aryl, arylalkyl, or cycloalkylalkyl.

In another embodiment, the compound of Formula (m), or a pharmaceutically acceptable salt thereof, is that wherein:

the first and second substituent are independently alkoxy, aryloxy or a group represented by the formula (a), (c), (d), (e), or (f);

R$_3$ and R$_4$ are hydrogen, alkyl, cycloalkyl, aryl, arylalkyl, or cycloalkylalkyl; and R$_5$ is hydrogen, alkyl, cycloalkyl, aryl, arylalkyl or cycloalkylalkyl.

5.4.4 Pharmaceutical Compositions Comprising a Compound of Formula (IV)

The present invention also encompasses compositions comprising a compound of Formula (IV), the compound of Formula (IV) being defined above, or a pharmaceutically acceptable salt thereof, and a pharmaceutically acceptable carrier or vehicle.

In one embodiment the compound of Formula (IV), or a pharmaceutically acceptable salt thereof, is that wherein the first or second substituent is present at the 5 or 7 position.

In a second embodiment, the compound of Formula (IV), or a pharmaceutically acceptable salt thereof, is that wherein the first and second substituent are independently alkyl, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (c), (d), (e), or (f).

In another embodiment, the compound of Formula (IV), or a pharmaceutically acceptable salt thereof, is that wherein:

the first and second substituent are independently alkoxy, aryloxy, hydroxy or a group represented by the formula (a), (c), (d), (e), or (f);

R$_3$ and R$_4$ are hydrogen, alkyl, cycloalkyl, aryl, arylalkyl, or cycloalkylalkyl; and R$_5$ is hydrogen, alkyl, cycloalkyl, alkoxycarbonylalkyl, aryl, arylalkyl, or cycloalkylalkyl.

In another embodiment, the compound of Formula (IV), or a pharmaceutically acceptable salt thereof, is that wherein:

the first and second substituent are independently alkoxy, aryloxy or a group represented by the formula (a), (c), (d), (e), or (f);

R$_3$ and R$_4$ are hydrogen, alkyl, cycloalkyl, aryl, arylalkyl, or cycloalkylalkyl; and R$_5$ is hydrogen, alkyl, cycloalkyl, aryl, arylalkyl or cycloalkylalkyl.

5.4.5 Pharmaceutical Compositions Comprising a Compound of Formula (V)

The present invention also encompasses compositions comprising a compound of Formula (V), the compound of Formula (V) being defined above, or a pharmaceutically acceptable salt thereof, and a pharmaceutically acceptable carrier or vehicle.

In one embodiment, the compound of Formula (V), or a pharmaceutically acceptable salt thereof, is that wherein the first or second substituent is present at the 5 or 7 position.

In another embodiment, the compound of Formula (V), or a pharmaceutically acceptable salt thereof, is that wherein the compound of Formula (V) is disubstituted and at least one of the substituents is a group represented by the formula (d) or (f).

5.4.6 Pharmaceutical Compositions Comprising a Compound of Formula (VI)

The present invention further provides pharmaceutical compositions comprising:

(A) a compound having the formula:

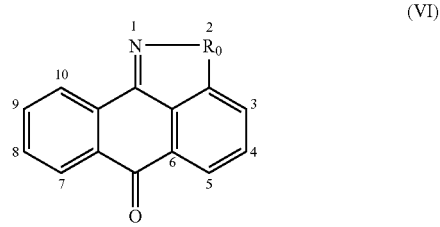

(VI)

or a pharmaceutically acceptable salt thereof, wherein R$_0$ is —O—, —S—, —S(O)—, —S(O)$_2$— or —CH$_2$—;

the compound being (i) unsubstituted, (ii) monosubstituted and having a first substituent, or (iii) disubstituted and having a first substituent and a second substituent;

the first or second substituent, when present, being at the 3, 4, 5, 7, 8, 9, or 10 position, wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

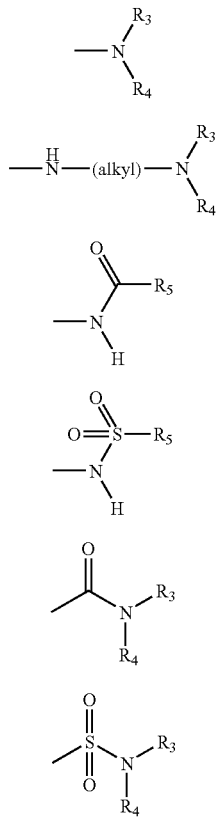

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl; and (B) a pharmaceutically acceptable carrier or vehicle.

In one embodiment, the first or second substituent of compounds of Formula VI, when present, are at the 3, 4, 5, 7, 8, 9, or 10 position, wherein the first and second substituent, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), (f):

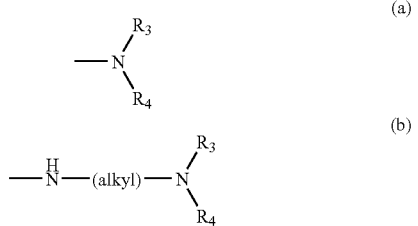

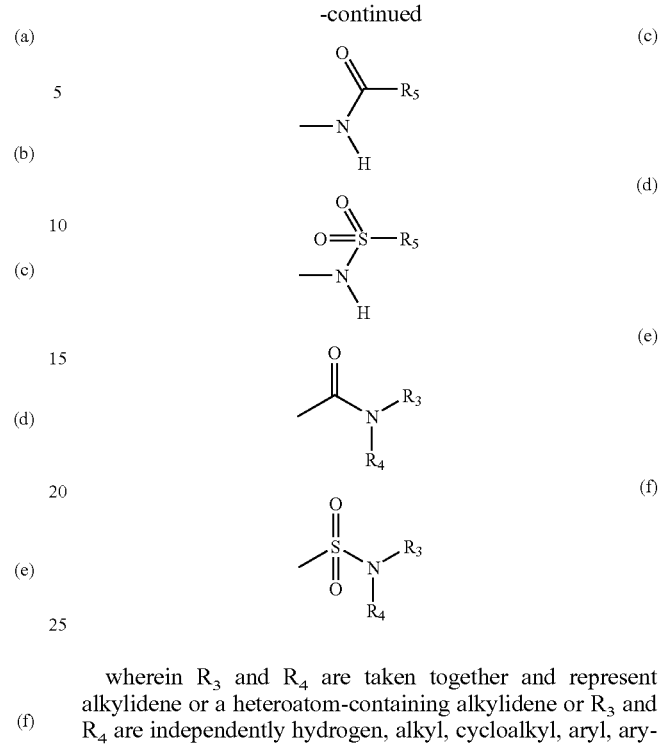

wherein R₃ and R₄ are taken together and represent alkylidene or a heteroatom-containing alkylidene or R₃ and R₄ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R₅ is hydrogen, alkyl, cycloalkyl, aryl, arylalkyl, cycloalkylalkyl, alkoxy, alkoxyalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl.

The present pharmaceutical compositions, which comprise a compound of Formula (I)-(V) or (VI), or a pharmaceutically acceptable salt thereof, (collectively "the present compositions") and a pharmaceutically acceptable carrier or vehicle, are useful for treating or preventing a disease associated with the modulation of JNK. Preferably, the present compositions are useful for inhibiting JNK. The present compositions are also useful for treating cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy; myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

5.5 Methods

The methods of the invention encompass treating or preventing a disease associated with the modulation of JNK, comprising administering to a patient in need thereof an effective amount of a compound of Formulas (I)-(VI), the compound of Formula (VI) being defined above, or a pharmaceutically acceptable salt thereof. The present invention also encompasses treating or preventing a disease, comprising administering to a patient in need thereof an effective amount of a compound of Formula (I)-(VI) or a pharmaceutically acceptable salt thereof, wherein the disease is cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy; myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

5.5.1 Methods Comprising Administering a Compound of Formula (I)

The present methods of the invention also encompass administering to a patient in need thereof an effective amount of a compound of Formula (I), the compound of Formula (I) being defined above, or a pharmaceutically acceptable salt thereof.

In one embodiment of the methods of the invention, the compound of Formula (I), or a pharmaceutically acceptable salt thereof, is that wherein the first or second substituent is present at the 5, 7, or 9 position. Preferably, the first or second substituent is present at the 5 or 7 position In another embodiment of the methods of the invention, the compound of Formula (I), or a pharmaceutically acceptable salt thereof, is that wherein:

the first or second substituent is present at the 5, 7, or 9 position;

the first and second substituent are independently alkoxy, aryloxy, hydroxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonylalkyl or cycloalkylalkyl.

In another embodiment of the methods of the invention, the compound of Formula (I), or a pharmaceutically acceptable salt thereof, is that wherein:

the first or second substituent is present at the 5, 7, or 9 position;

the first and second substituent are independently alkoxy, aryloxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, or cycloalkylalkyl.

5.5.2 Methods Comprising Administering a Compound of Formula (II)

The present methods of the invention also encompass administering to a patient in need thereof an effective amount of a compound of Formula (II), the compound of Formula (II) being defined above, or a pharmaceutically acceptable salt thereof.

In one embodiment of the methods of the invention, the compound of Formula (II), or a pharmaceutically acceptable salt thereof, is that wherein the first or second substituent, when present, is present at the 5, 7, or 9 position. Preferably, the first or second substituent is present at the 5 or 7 position In another embodiment of the methods of the invention, the compound of Formula (II), or a pharmaceutically acceptable salt thereof, is that wherein:

the first and second substituent are independently alkoxy, aryloxy, hydroxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonylalkyl or cycloalkylalkyl.

In another embodiment of the methods of the invention, the compound of Formula (II), or a pharmaceutically acceptable salt thereof, is that wherein:

the first and second substituent are independently alkoxy, aryloxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl or cycloalkylalkyl.

5.5.3 Methods Comprising Administering a Compound of Formula (III)

The present methods of the invention also encompass administering to a patient in need thereof an effective amount of a compound of Formula (III), the compound of Formula (III) being defined above, or a pharmaceutically acceptable salt thereof.

In one embodiment of the methods of the invention, the compound of Formula (III), or a pharmaceutically acceptable salt thereof, is that wherein the first or second substituent is present at the 5, 7, or 9 position. Preferably, the first or second substituent is present at the 5 or 7 position In another embodiment of the methods of the invention, the compound of Formula (III), or a pharmaceutically acceptable salt thereof, is that wherein:

the first and second substituent are independently alkoxy, aryloxy, hydroxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonylalkyl or cycloalkylalkyl.

In another embodiment of the methods of the invention, the compound of Formula (III), or a pharmaceutically acceptable salt thereof, is that wherein:

the first and second substituent are independently alkoxy, aryloxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl or cycloalkylalkyl.

5.5.4 Method Comprising Administering a Compound of Formula (IV)

The present methods of the invention also encompass administering to a patient in need thereof an effective amount of a compound of Formula (IV), the compound of Formula (IV) being defined above, or a pharmaceutically acceptable salt thereof.

In one embodiment of the methods of the invention, the compound of Formula (IV), or a pharmaceutically acceptable salt thereof, is that wherein the first or second substituent is present at the 5 or 7 position In a second embodiment of the methods of the invention, the compound of Formula (IV), or a pharmaceutically acceptable salt thereof, is that wherein the first and second substituent are independently alkyl, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (c), (d), (e), or (f).

In another embodiment of the methods of the invention, the compound of Formula (IV), or a pharmaceutically acceptable salt thereof, is that wherein:

the first and second substituent are independently alkoxy, aryloxy, hydroxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonylalkyl or cycloalkylalkyl.

In another embodiment of the methods of the invention, the compound of Formula (IV), or a pharmaceutically acceptable salt thereof, is that wherein:

the first and second substituent are independently alkoxy, aryloxy or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl or cycloalkylalkyl.

5.5.5 Methods Comprising Administering a Compound of Formula (V)

The present methods of the invention also encompass administering to a patient in need thereof an effective amount of a compound of Formula (V), the compound of Formula (V) being defined above, or a pharmaceutically acceptable salt thereof.

In one embodiment of the methods of the invention, the compound of Formula (V), or a pharmaceutically acceptable salt thereof, is that wherein the first or second substituent is present at the 5 or 7 position In one embodiment of the methods of the invention, the compound of Formula (V), or a pharmaceutically acceptable salt thereof, is that wherein the compound of Formula (V) is disubstituted and at least one of the substituents is a group represented by the formula (d) or (f).

While the invention contemplates modulating all JNK, modulation of JNK which is expressed in the brain is important for treating central or peripheral neurological degenerative disorders like epilepsy, Alzheimer's disease, Parkinson's disease, Huntington's disease, amyotrophic laterial sclerosis, peripheral neuropathy, and spinal cord damage. Thus, in a preferred embodiment of the methods of the invention, the disease that is treated or prevented is a central or peripheral neurological degenerative disorder, wherein the central or peripheral neurological degenerative disorder is epilepsy, Alzheimer's disease, Parkinson's disease, Huntington's disease, amyotrophic laterial sclerosis, peripheral neuropathy, or spinal cord damage.

The methods of the invention are also useful for treating or preventing cancer; rheumatoid arthritis; rheumatoid spondylitis; osteoarthritis; gout; asthma; bronchitis; cystic fibrosis; inflammatory bowel disease; irritable bowel syndrome; mucous colitis; ulcerative colitis; Crohn's disease; gastritis; esophagitis; hepatitis; multiple sclerosis; endotoxin shock; psoriasis; eczema; dermatitis; atherosclerosis; restenosis following angioplasty; left ventricular hypertrophy, myocardial infarction; stroke; ischemic damage to the heart, kidney, liver, or brain; transplant rejection; systemic lupus erythomatosus; pancreatitis; chronic obstructive pulmonary disease; conjunctive heart failure or a central or peripheral neurological degenerative disorder.

Preferably, the compound of Formula (I)-(VI) is:

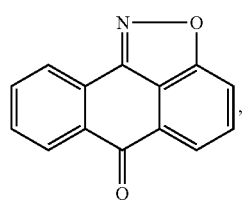

(Compound AA)

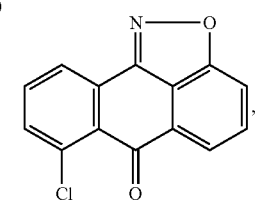

(Compound AB)

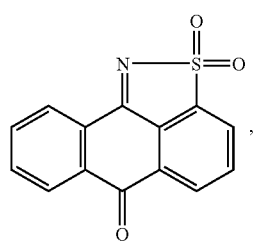

(Compound AC)

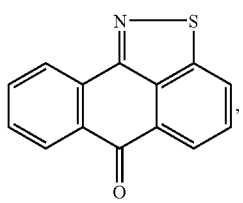

(Compound AD)

-continued
(Compound AE)
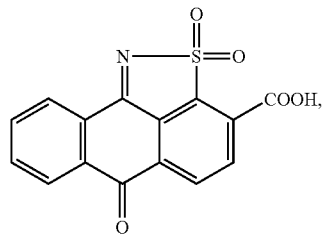
(Compound AF)
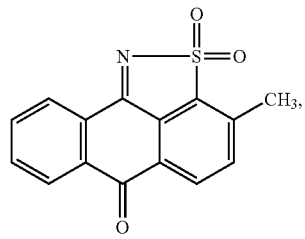
(Compound AG)
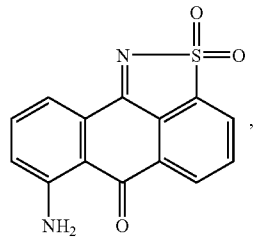
(Compound AH)
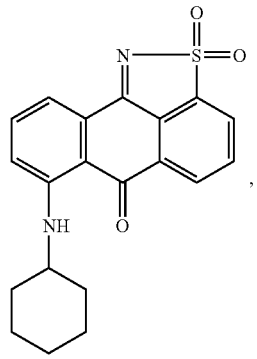
(Compound AI)
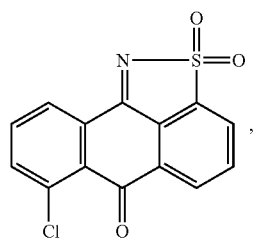
(Compound AJ)
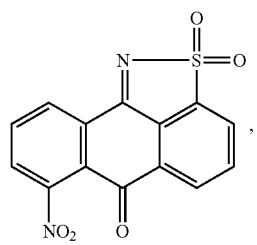
(Compound AK)
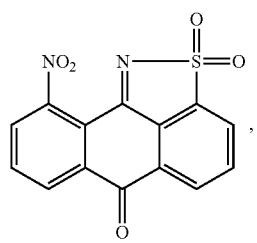
(Compound AL)
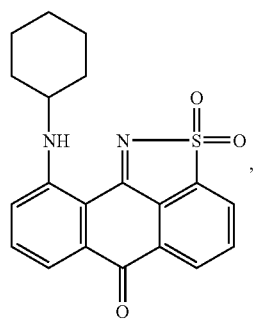
(Compound AM)
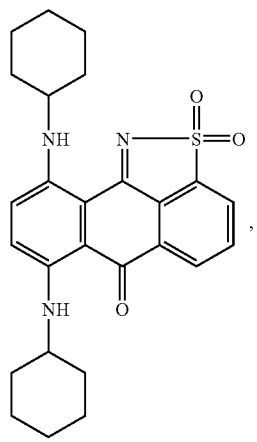
(Compound AN)
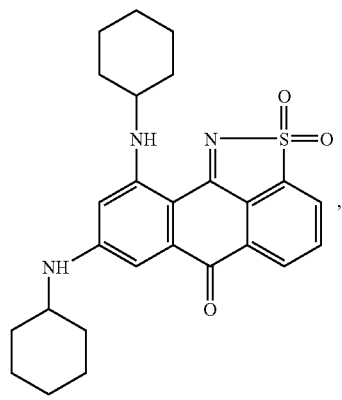

-continued
(Compound AO)
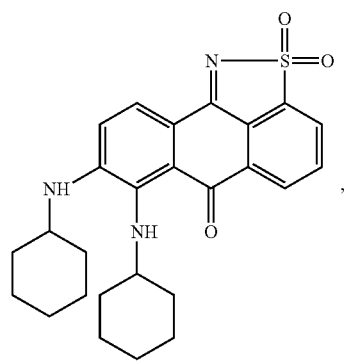
(Compound AP)
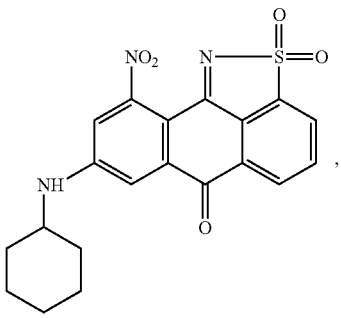
(Compound AQ)
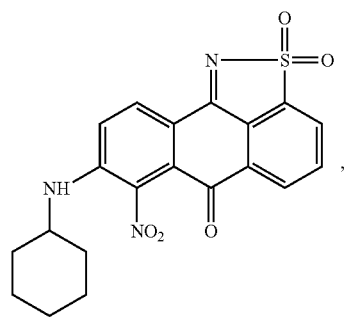
(Compound AR)
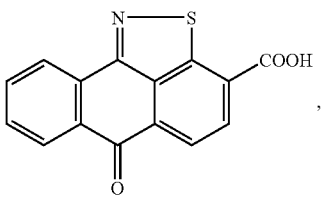
(Compound AS)
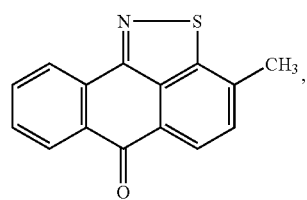
(Compound AT)
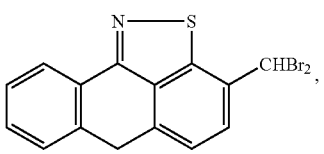
(Compound AU)
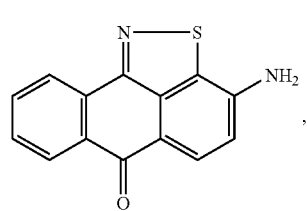
(Compound AV)
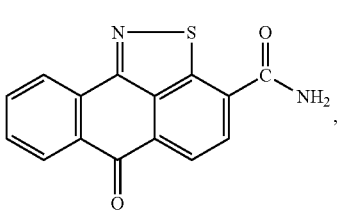
(Compound AW)
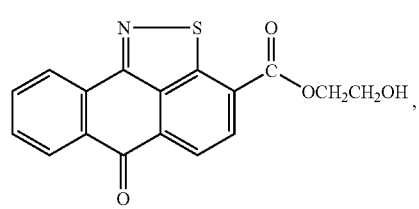
(Compound AX)
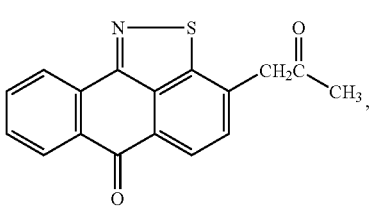
(Compound AY)
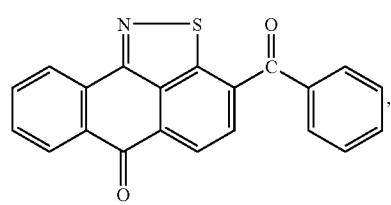
(Compound AZ)
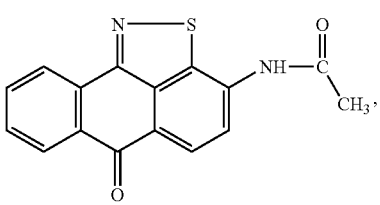

-continued
(Compound BA)
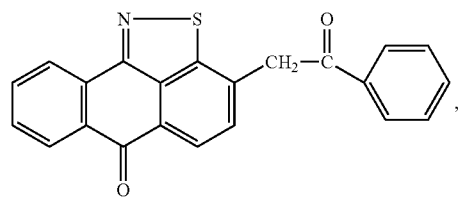
(Compound BB)
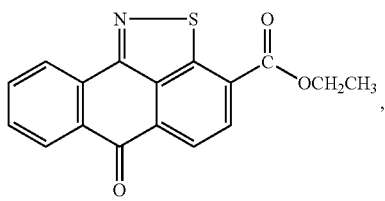
(Compound BC)
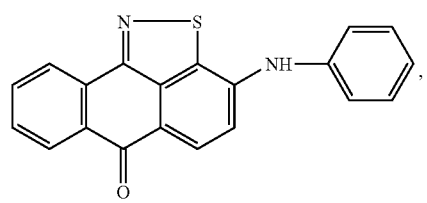
(Compound BD)
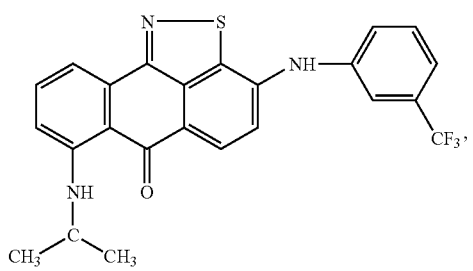
(Compound BE)
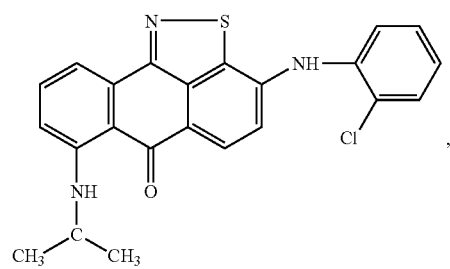
(Compound BF)
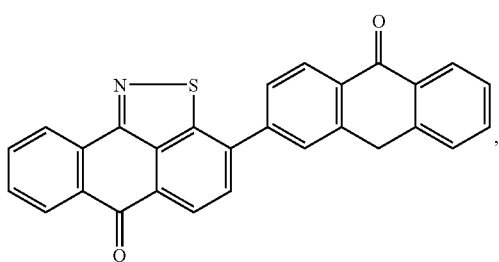
(Compound BG)
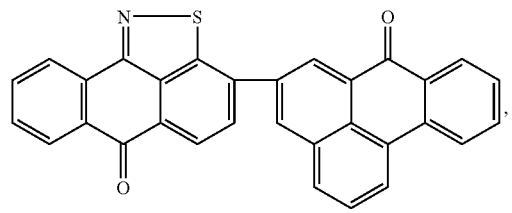
(Compound BH)
(Compound BI)
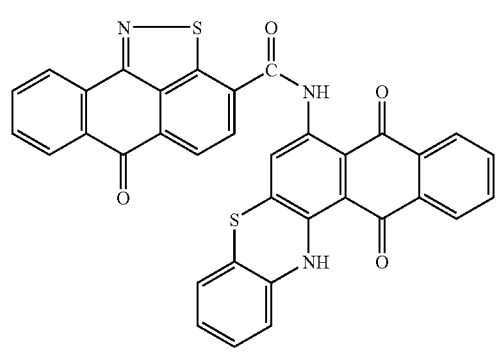
(Compound BJ)
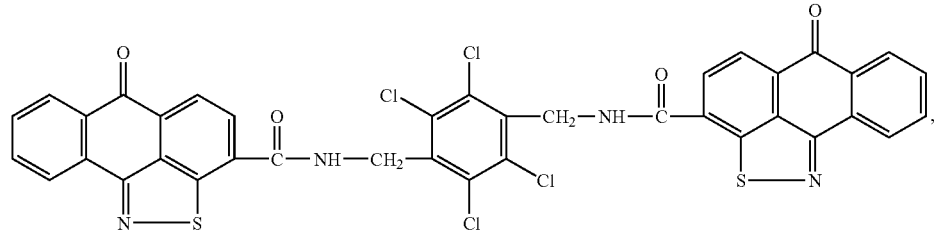

-continued
(Compound BK)
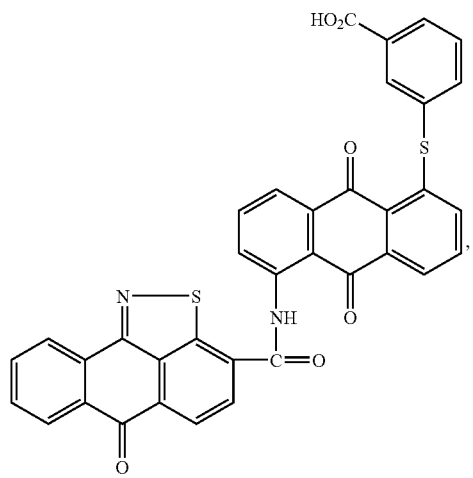
(Compound BL)
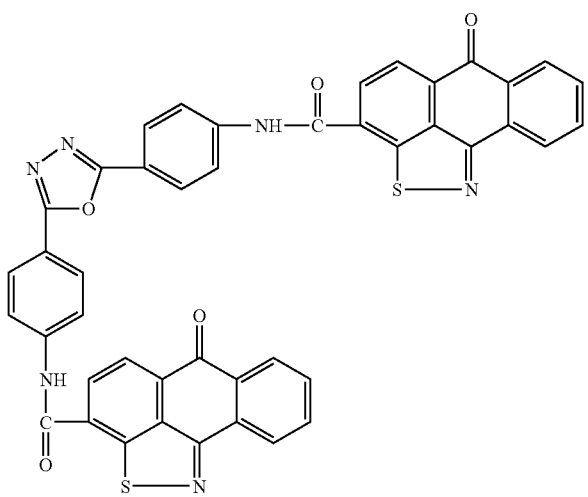
(Compound BM)
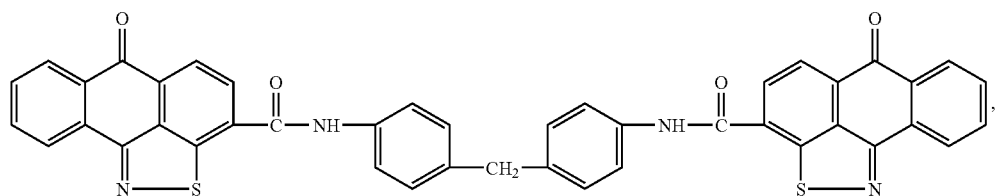
(Compound BN)
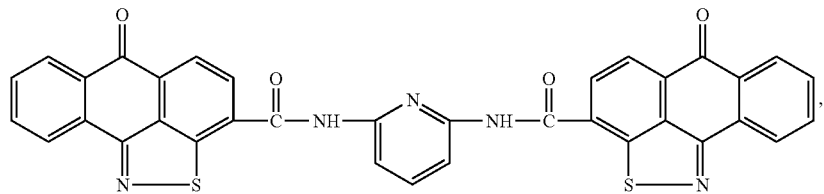
(Compound BO)
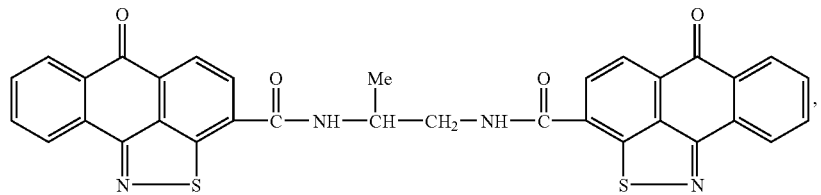
(Compound BP)
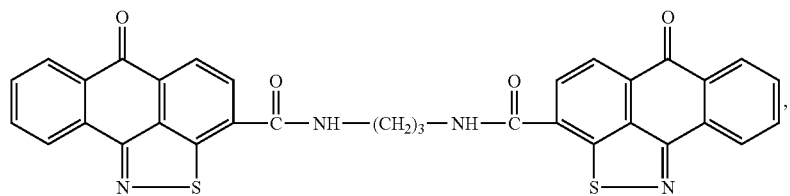
(Compound BQ)
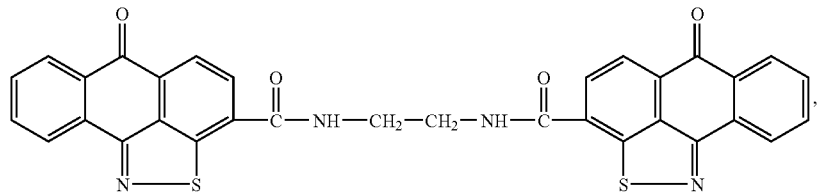

-continued
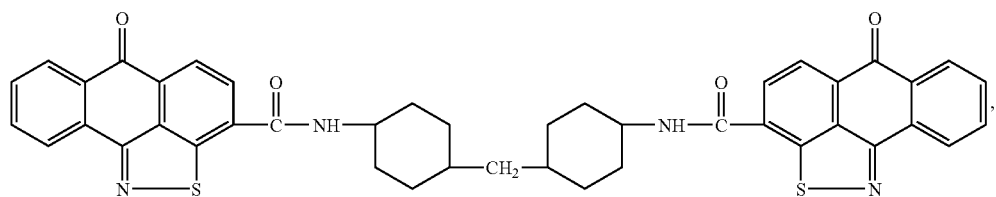
(Compound BR)
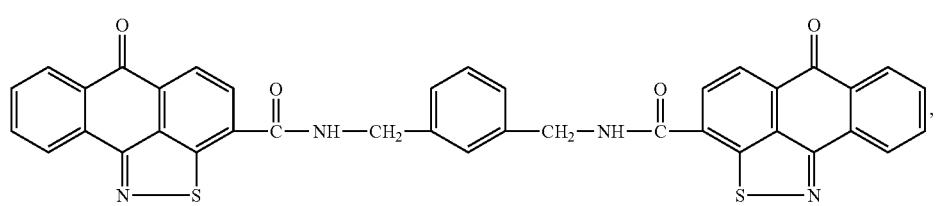
(Compound BS)
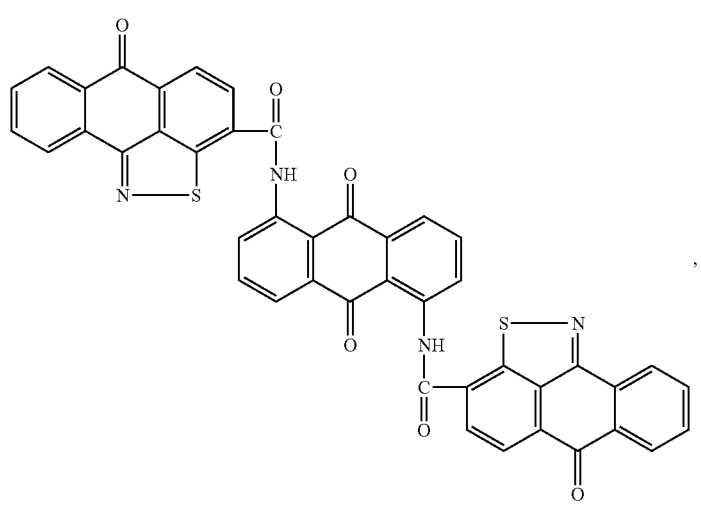
(Compound BT)
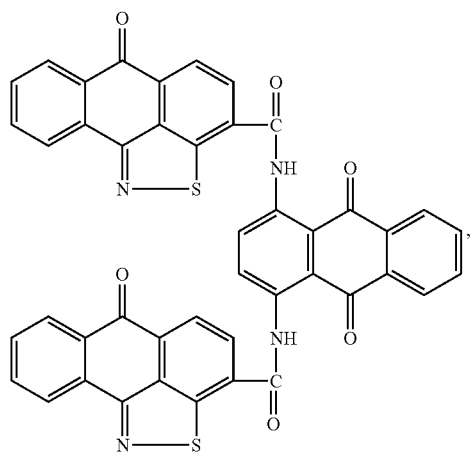
(Compound BU)
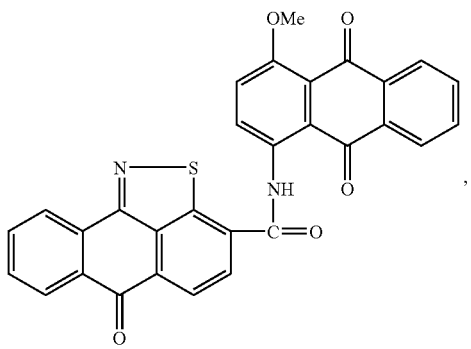
(Compound BW)

-continued
(Compound BV)
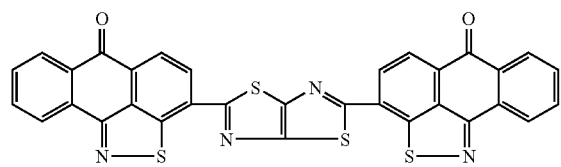
(Compound BX)
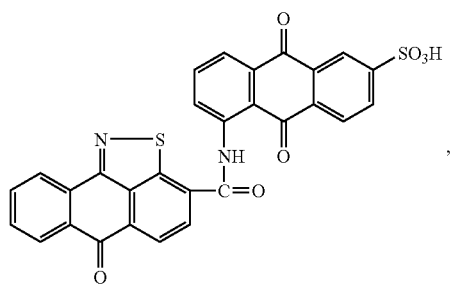
(Compound BY)
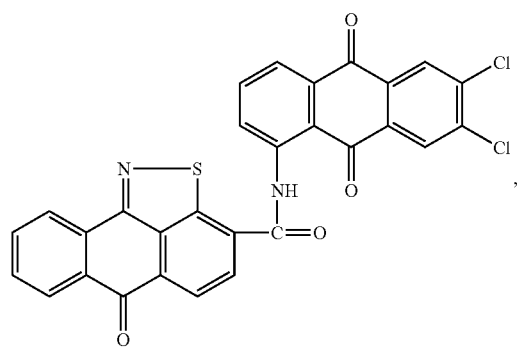
(Compound BZ)
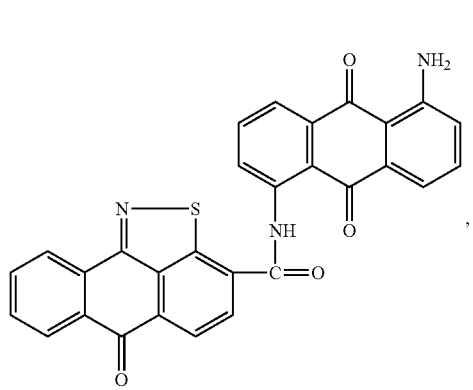
(Compound CA)
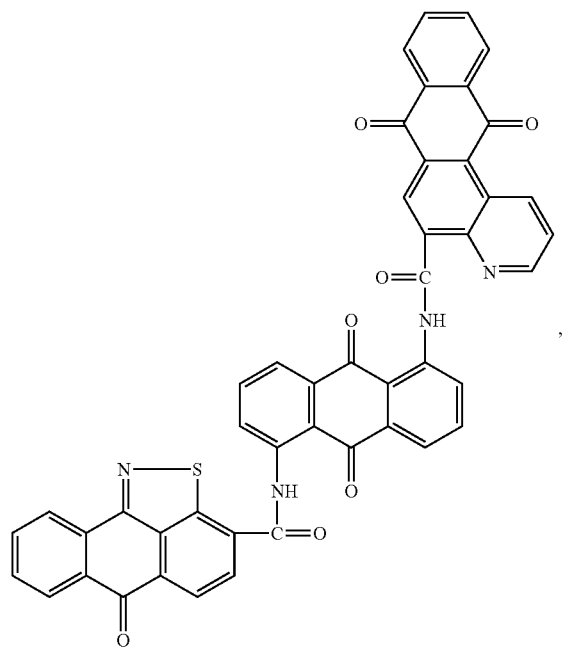
(Compound CB)
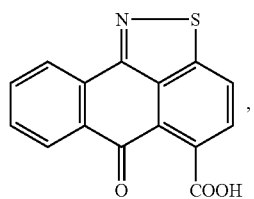
(Compound CC)
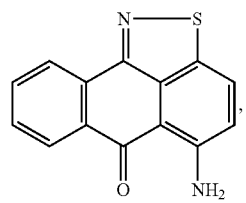
(Compound CD)
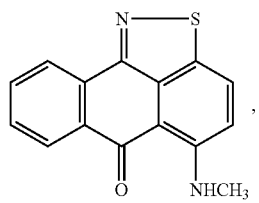

-continued
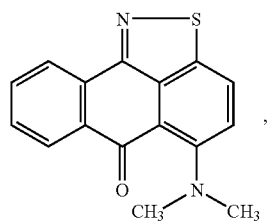
(Compound CE)
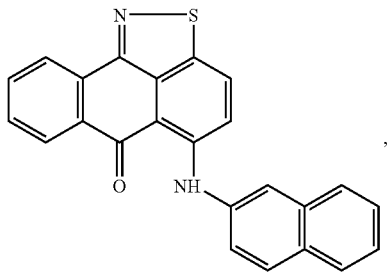
(Compound CF)
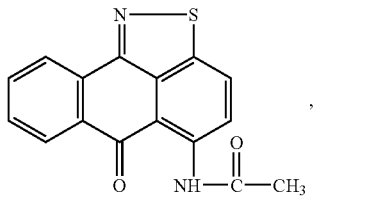
(Compound CG)
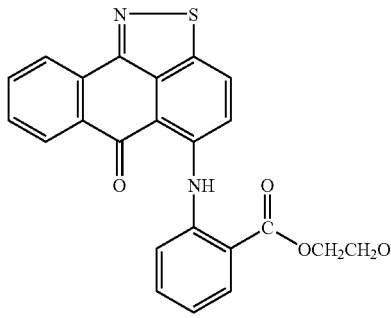
(Compound CH)
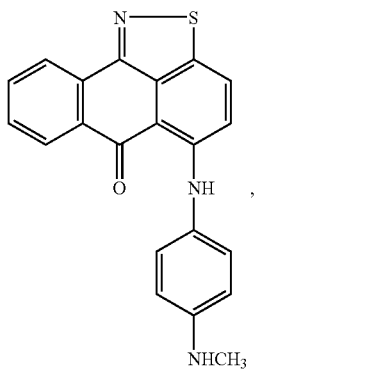
(Compound CI)
(Compound CJ)
(Compound CK)
(Compound CL)
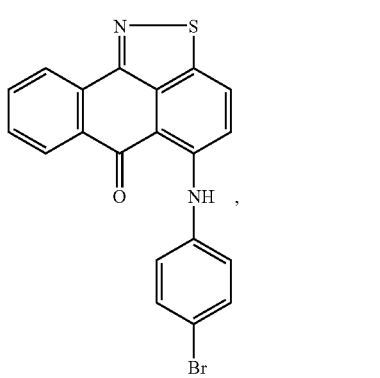
(Compound CM)
(Compound CN)

-continued
(Compound CO) 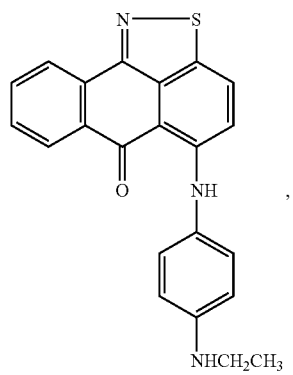 , (Compound CP) 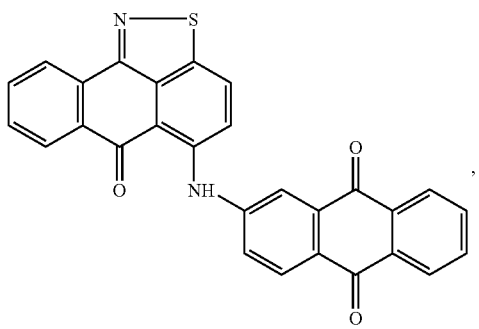 ,
(Compound CQ) (Compound CR)
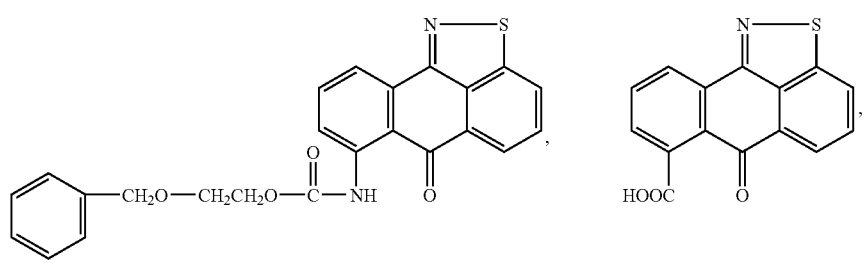
(Compound CS) (Compound CT)
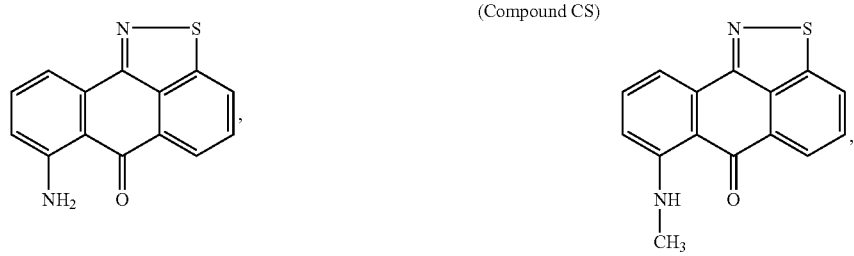
(Compound CU) (Compound CV)
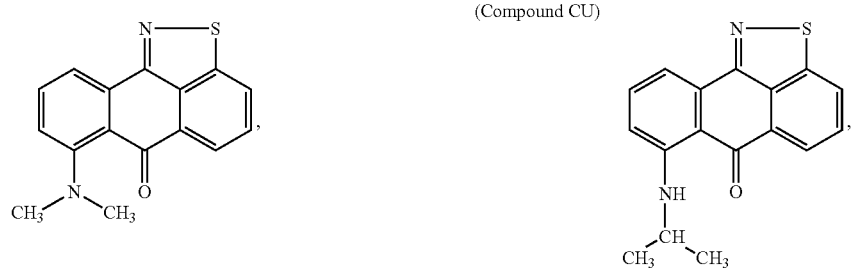

-continued
(Compound CW)
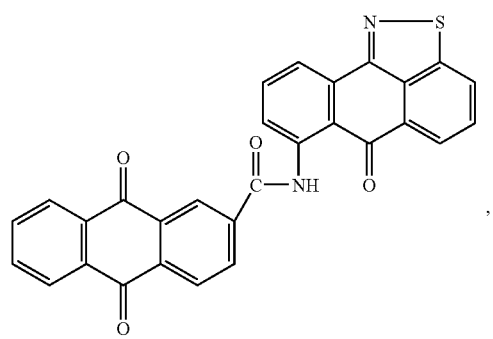
(Compound CX)
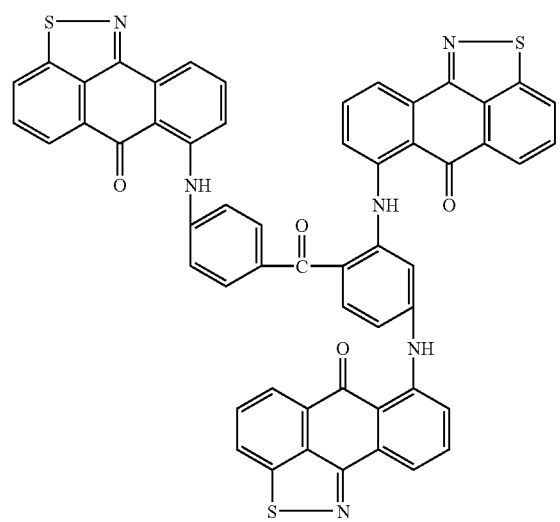
(Compound CY)
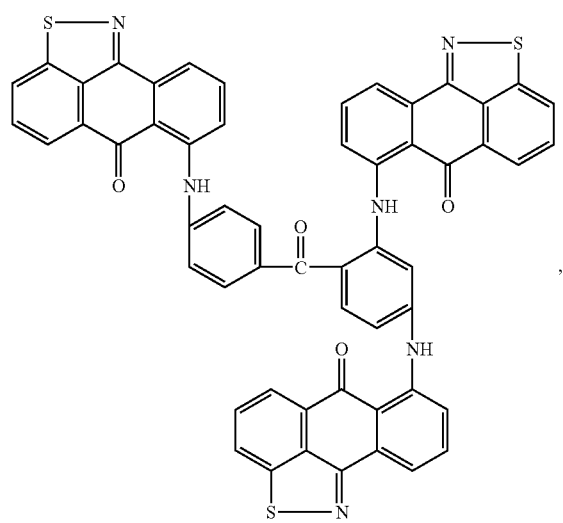
(Compound CZ)
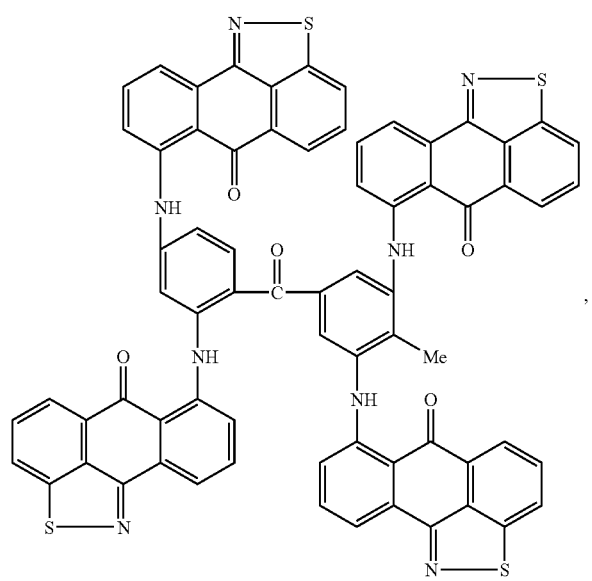

-continued
(Compound DA)
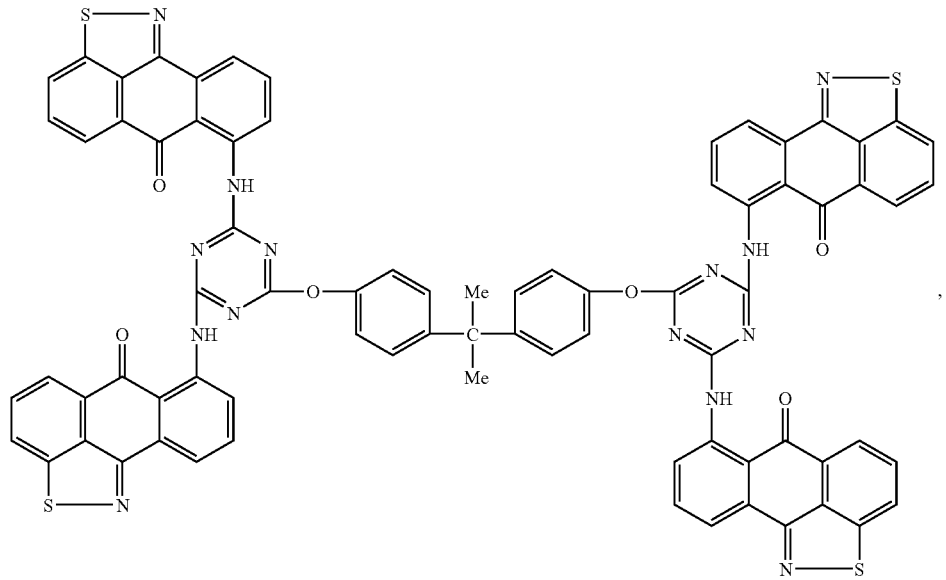
(Compound DB)     (Compound DC)
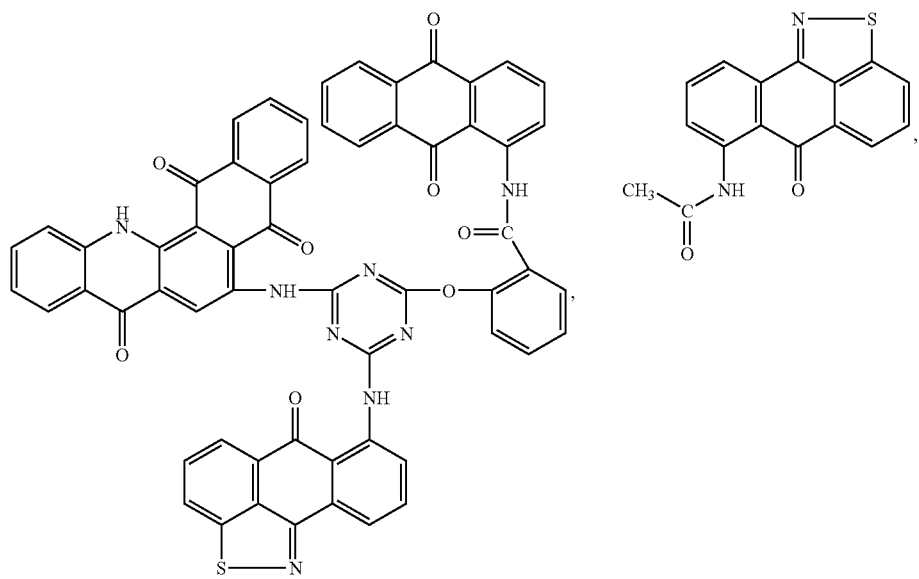
(Compound DD)     (Compound DE)
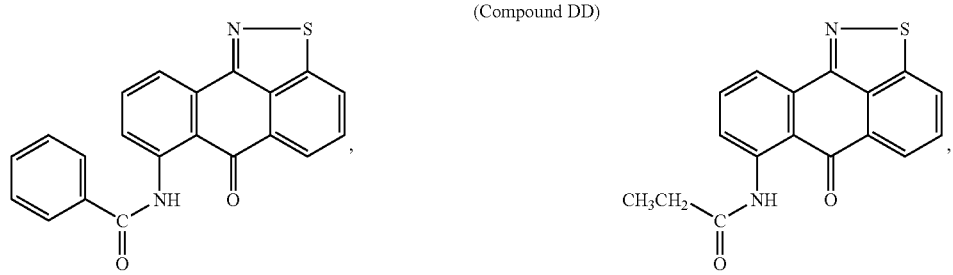

-continued
(Compound DF)
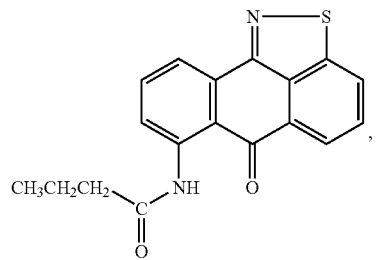
(Compound DG)
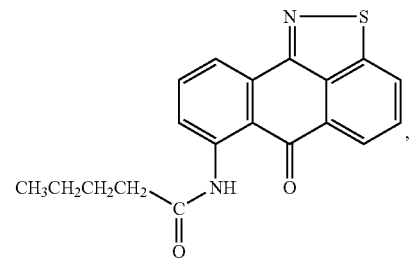
(compound DH)
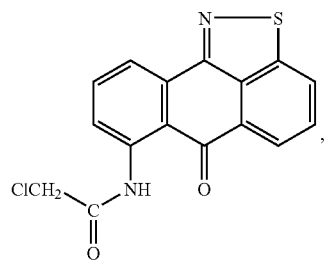
(Compound DI)
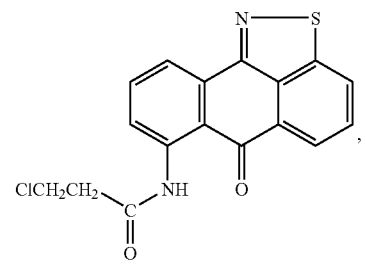
(Compound DJ)
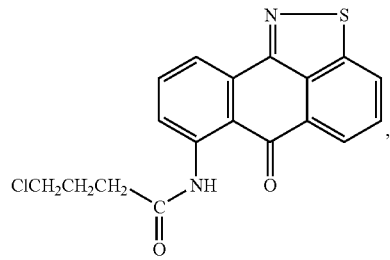
(Compound DK)
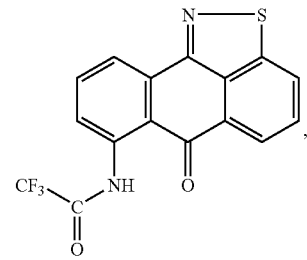
(Compound DL)
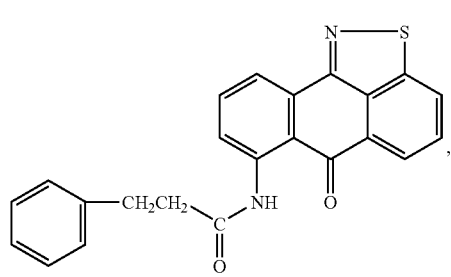
(Compound DM)
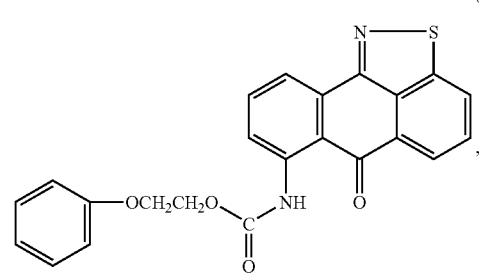
(Compound DN)
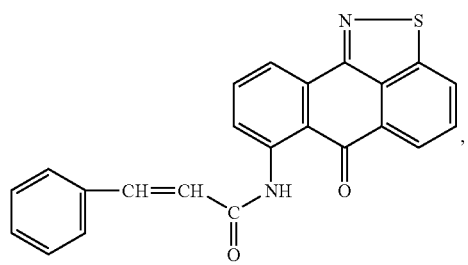
(Compound DO)
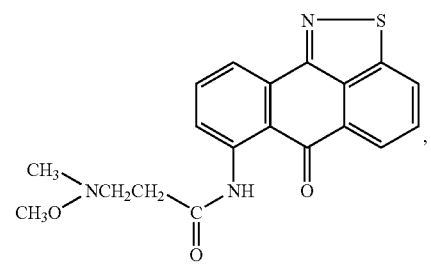

-continued
(Compound DP)
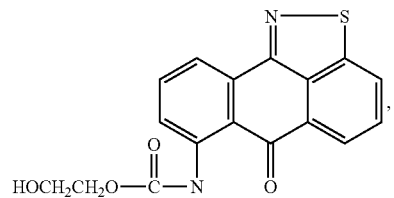
(compound DQ)
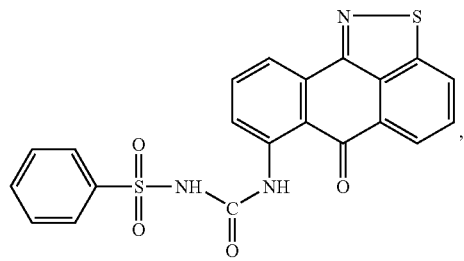
(Compound DR)
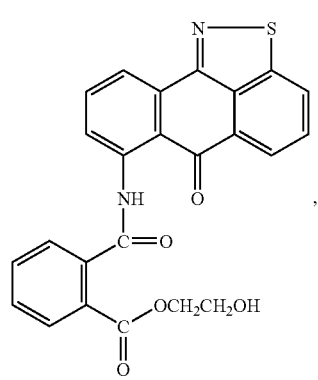
(Compound DS)
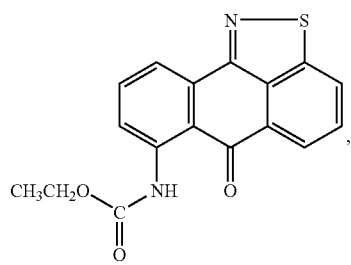
(Compound DT)
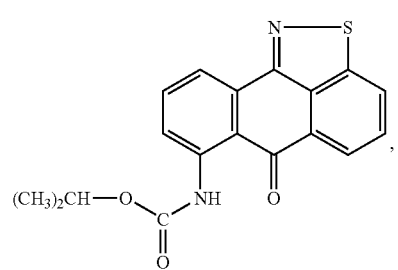
(Compound DU)
(Compound DV)
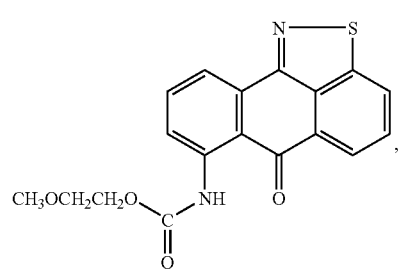
(Compound DW)
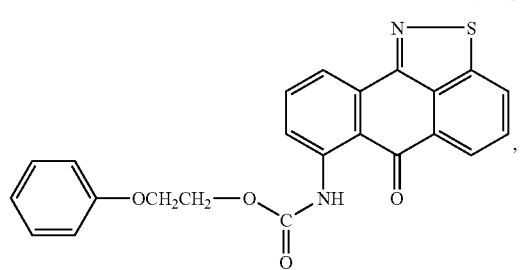
(Compound DX)
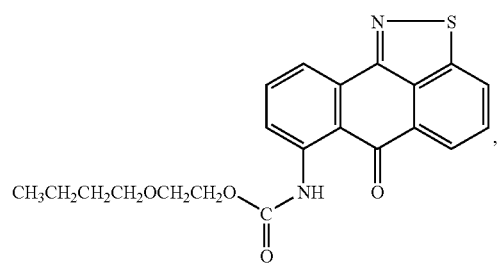
(Compound CY)

-continued
(Compound DZ)
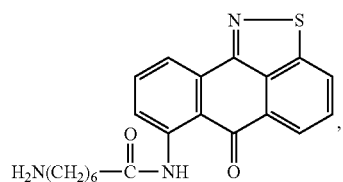
(Compound EA)
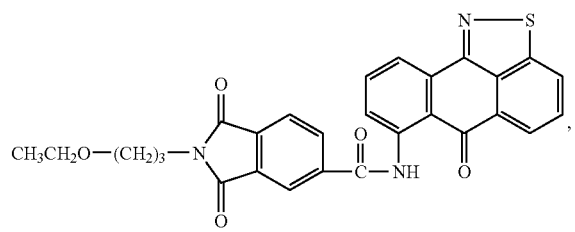
(Compound EB)
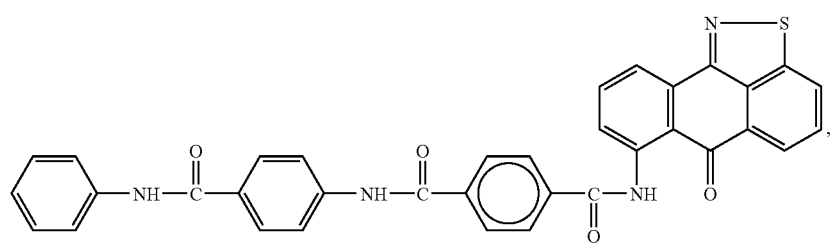
(Compound EC)
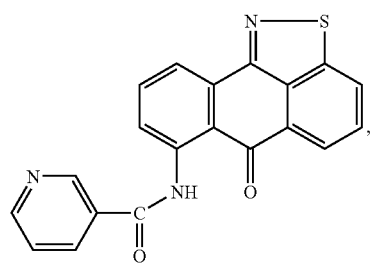
(Compound ED)
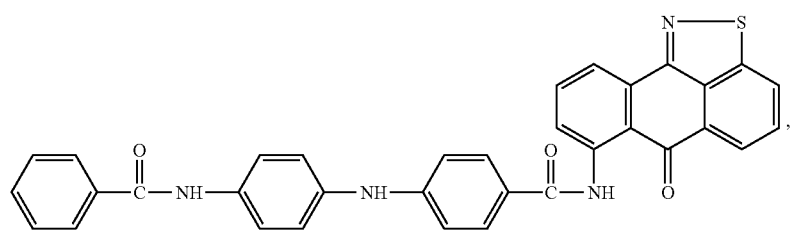
(Compound EE)
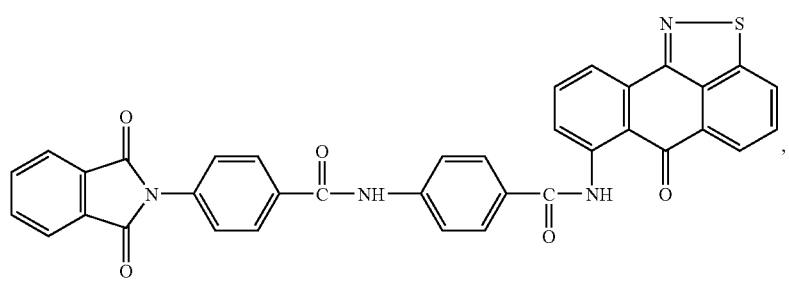
(Compound EF)
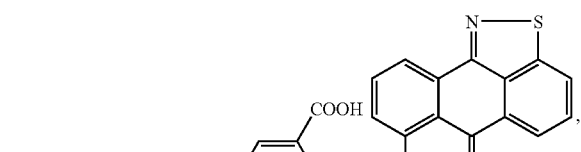
(Compound EG)
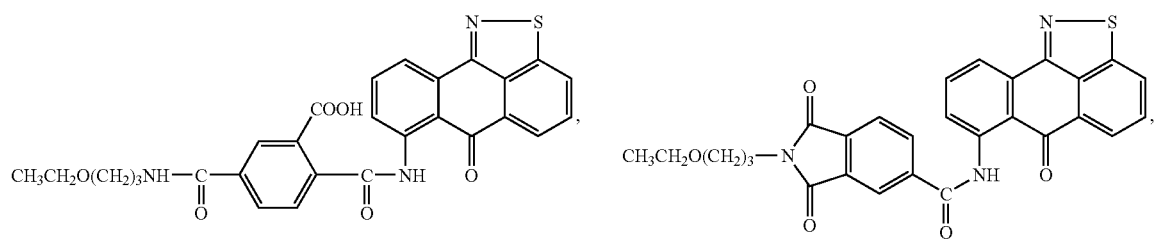

-continued
(Compound EH)
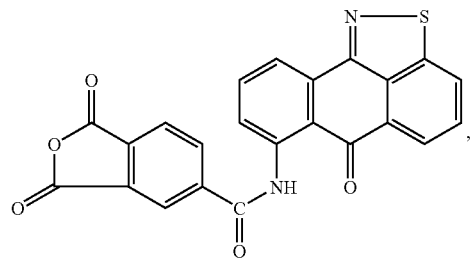
(Compound EI)
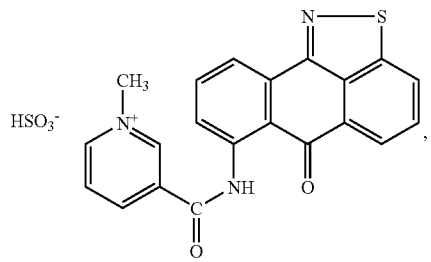
(Compound EJ)
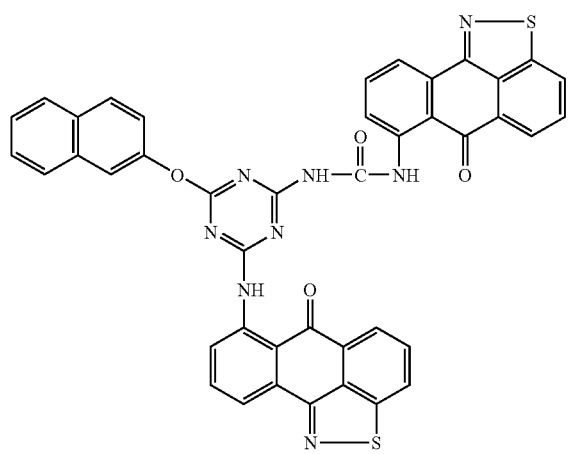
(Compound EK)
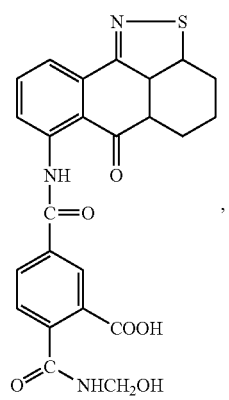
(Compound EL)
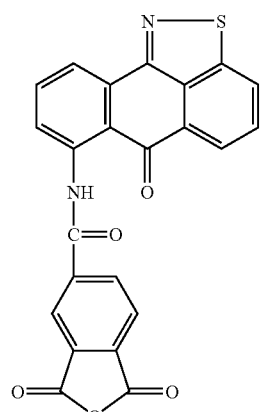
(Compound EM)
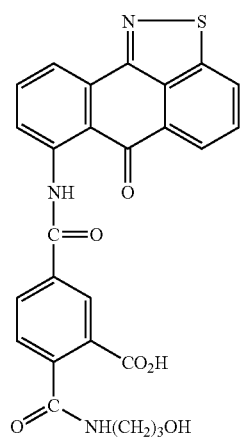
(Compound EN)
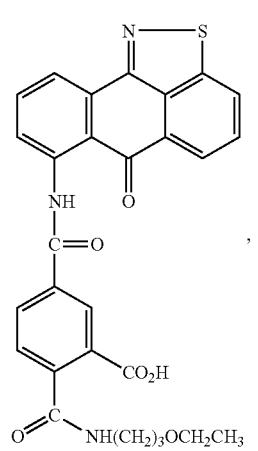
(Compound EO)
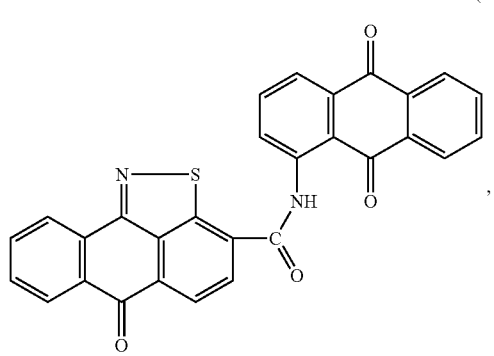

-continued
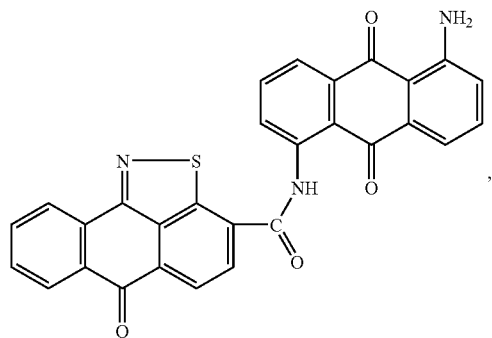
(Compound EP)
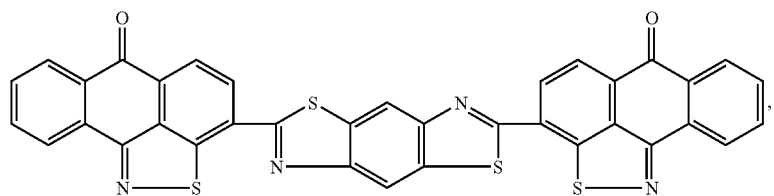
(Compound EQ)
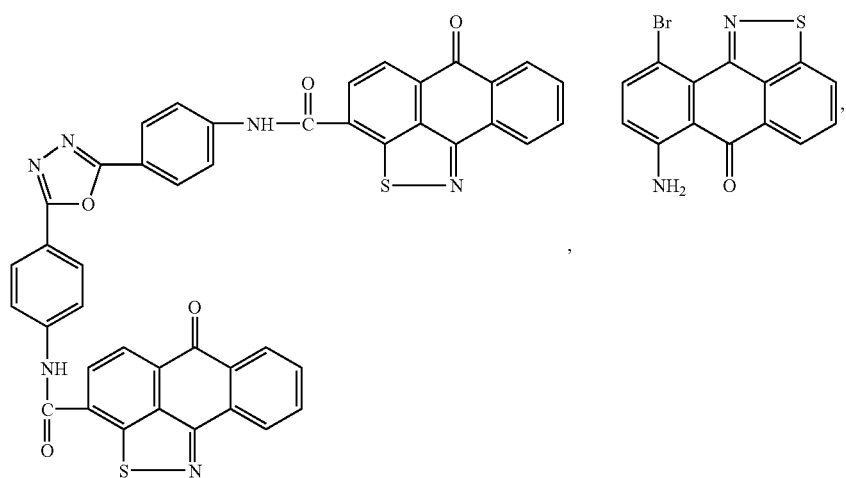
(Compound ER)
(Compound ES)
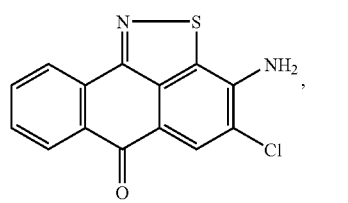
(Compound ET)
(Compound EU)
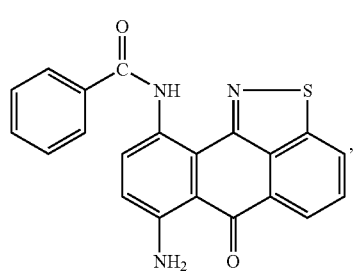
(Compound EV)
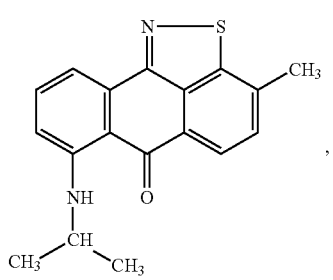
(Compound EW)

-continued
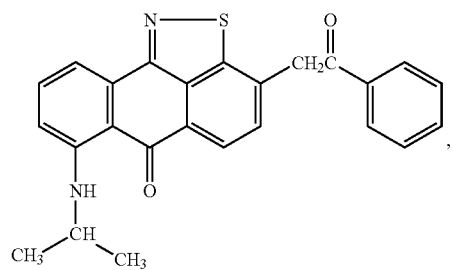 (Compound EX)
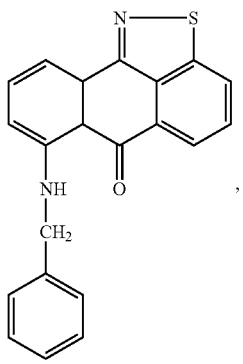 (Compound EY)
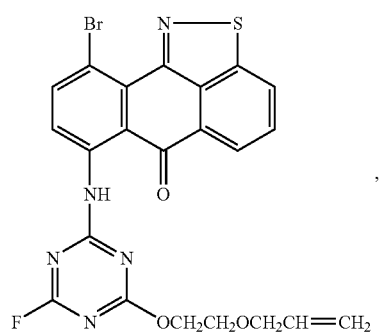 (Compound EZ)
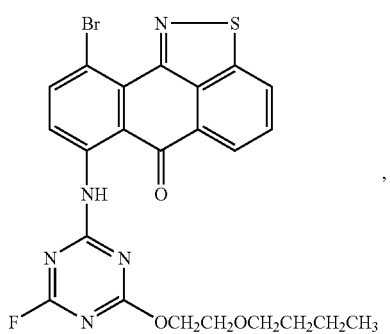 (Compound FA)
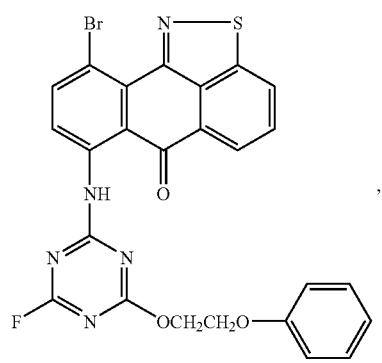 (Compound FB)
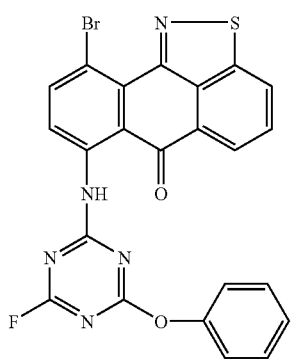 (Compound FC)
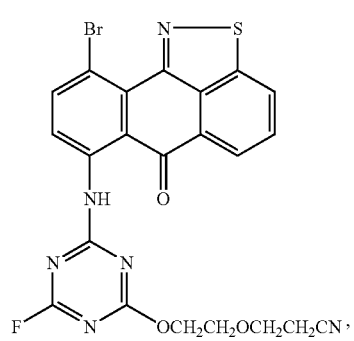 (Compound FD)
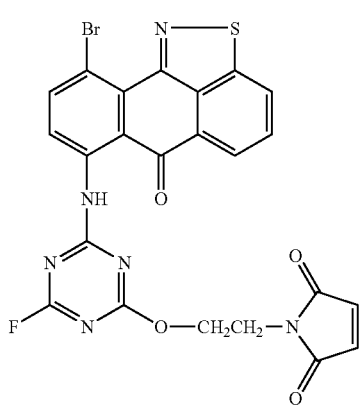 (Compound FE)

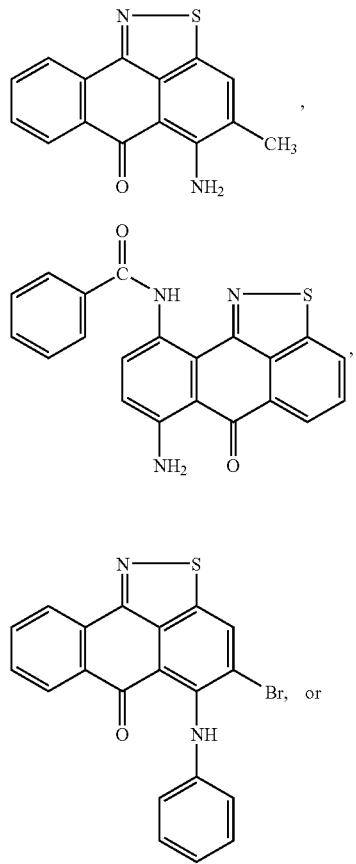
(Compound FF)
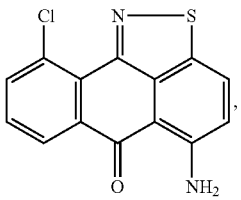
(Compound FG)
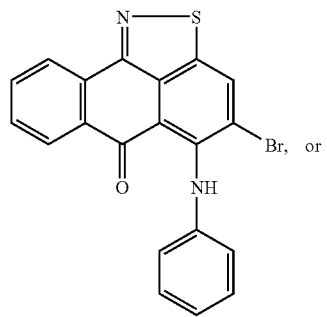
(Compound FH)
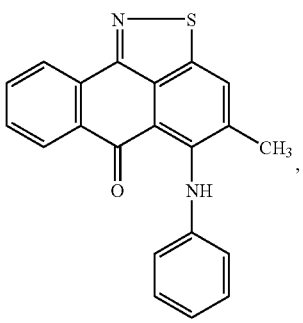
(Compound FI)
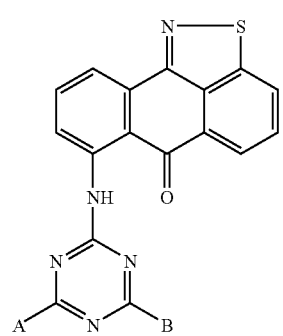 Br, or
(Compound FJ)
a compound of formula VII:
(VII)
wherein A and B are:
| A | B | Compound |
|---|---|---|
| —NH$_2$ | —NH$_2$ | FK |
| —N(CH$_2$CH$_2$CH$_2$CH$_3$)$_2$ | —N(CH$_2$CH$_2$CH$_2$CH$_3$)$_2$ | FL |
| —NHC$_6$H$_5$ | —NHC$_6$H$_5$ | FM |
| —OC$_6$H$_5$ | —OC$_6$H$_5$ | FN |
| —NH$_2$ | —N(CH$_2$CH$_2$CH$_2$CH$_3$)$_2$ | FO |
| —NH$_2$ | —N(CH$_2$CH$_2$CN)(CH$_2$CH$_2$OH) | FP |
| —NH$_2$ | —N(CH$_2$CH$_2$CH$_2$CH$_3$)$_2$ | FQ |

-continued

| A | B | Compound |
|---|---|---|
| —NHCH₃ | —NHCH₃ | FR |
| —N(CH₃)₂ | —N(CH₃)₂ | FS |
| —N(CH₂CH₃)₂ | —N(CH₂CH₃)₂ | FT |
| —NHCH₂CH₃ | —NHCH₂CH₃ | FU |
| —OCH₃ | —OCH₃ | FV |
| —OCH₂CH₃ | —OCH₂CH₃ | FW |
| —OCH₂CH₂OCH₃ | —OCH₂CH₂OCH₃ | FX |
| 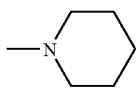 | 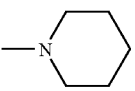 | FY |
| —Cl | —Cl | FZ |
| —NHCH₂CH₂OH | —NHCH₂CH₂OH | GA |
| —NHCH₂CH₂CH₃ | —NHCH₂CH₂CH₃ | GB |
| —F | —OCH₂CH₂CH₂CH₃ | GC |
| —F | —OCH(CH₃)₂ | GD |
| —F | —OCH₂CH(CH₂CH₃)CH₂CH₂CH₂CH₃ | GE |
| —F | —OCH₂CH₂OC₆H₅ | GF |
| —F | —OCH₂CH=CH₂ | GG |
| —F | —OCH₂CHCN | GH |
| —F | —O(CH₂)₃OCH₃ | GI |
| —F | —O(CH₂)₂O(CH₂)₂OCH₃ | GJ |
| —F | —OCH₂C₆H₅ | GK |
| —F | —OCH₂CH₂OH | GL |
| —F | —OCH₂(4-chlorophenyl) | GM |
| —F | —OCH₂CH₂Cl | GN |
| —F | —OCH₂CH₂OCH₂CH₂CH₃ | GO |
| —F | —O(CH₂)₅CH₃ | GP |
| —F | 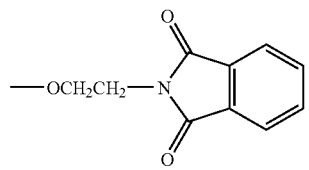 | GQ |
| —F | 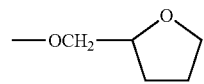 | GR |
| —F | —OCH₂CH(OH)CH₂OCH₃ | GS |
| —F | —OCH₂CH₂OC(O)C₆H₅ | GT |
| —F | —OCH₂CH₂OCH₂C₆H₅ | GU |
| —F | —OCH₂C(O)OCH₂CH₂C=CH₂ | GV |
| —F | —OCH₂CH₂OCH₃ | GW |
| —F | —OCH₂CH₂C₆H₅ | GX |
| —F | —OCH₃ | GY |
| —F | —OCH₂CH₂OCH₂CH₂CN | GZ |
| —Cl | —NHCH₂CH₂OCH₂CH₂OCH₂CH₂CH₃ | HA |
| —OCH₂CH₂CH₃ | —NHCH₂CH₂OCH₂CH₂OCH₂CH₂CH₃ | HB |
| 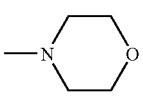 | 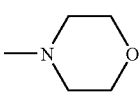 | HC |

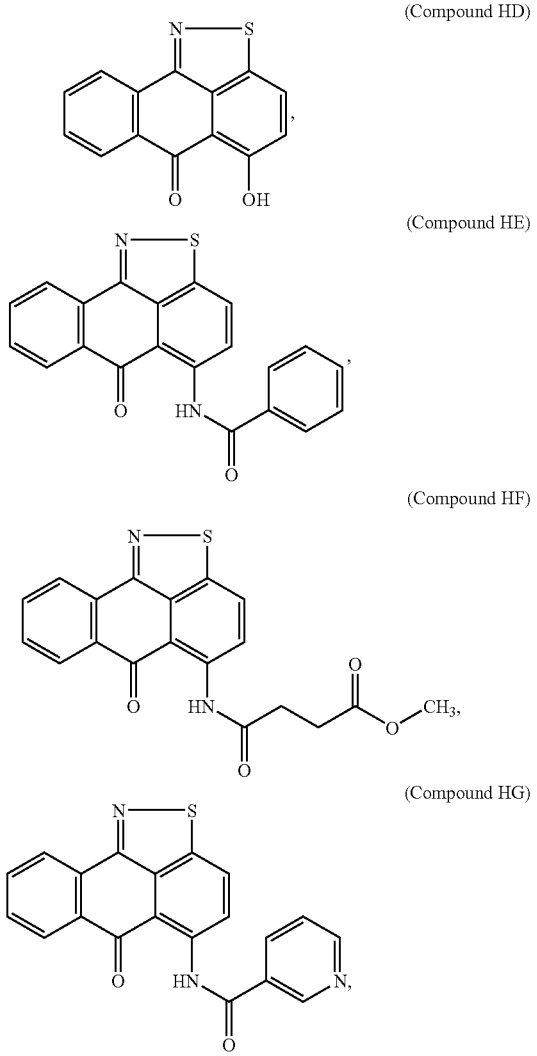

(Compound HD)

(Compound HE)

(Compound HF)

(Compound HG)

or a pharmaceutically acceptable salt thereof.

More preferably, the compound of Formula (VI) is Compound CC, or a pharmaceutically acceptable salt thereof.

5.6 Therapeutic/Prophylactic Administration

When administered to a patient, e.g., an animal for veterinary use or to a human for clinical use, the compounds of Formula (I)-(VI), or pharmaceutically acceptable salts thereof, are preferably in isolated form. By "isolated" it is meant that prior to administration, a compound of Formula (I)-(VI), or a pharmaceutically acceptable salt thereof, is separated from other components of a synthetic organic chemical reaction mixture or natural product source, e.g., plant matter, tissue culture, or bacterial broth. Preferably, the compounds of Formula (I)-(VI), or pharmaceutically acceptable salts thereof, are isolated via conventional techniques, e.g., extraction followed by chromatography, recrystalization, or another conventional technique. When in isolated form, the compounds of Formula (I)-(VI), or pharmaceutically acceptable salts thereof, are at least 90%, preferably at least 95%, of a compound of Formula (I)-(VI), or a pharmaceutically acceptable salt thereof, by weight of that which is isolated. "Single compound of Formula (I)-(VI), or a pharmaceutically acceptable salt thereof," as used herein, means a compound of Formula (I)-(VI) and racemates and/or enantiomers thereof, and pharmaceutically acceptable salts thereof.

The invention provides methods of treatment and prophylaxis by administration to a patient of an effective amount of a compound of Formula (I)-(VI), or a pharmaceutically acceptable salt thereof. The patient is preferably an animal, including, but not limited to, an animal such as a cow, horse, sheep, pig, chicken, turkey, quail, cat, dog, mouse, rat, rabbit, or guinea pig and is more preferably a mammal, and most preferably a human.

The present pharmaceutical compositions, which comprise one or more of the compounds of Formula (I)-(VI), or pharmaceutically acceptable salts thereof, can be administered by any convenient route, for example by infusion or bolus injection, by absorption through epithelial or mucocutaneous linings (e.g., oral mucosa, rectal and intestinal mucosa) and can be administered together with another biologically active agent. Administration can be systemic or local. Various delivery systems are known, e.g., encapsulation in liposomes, microparticles, microcapsules, and capsules, and can be used to administer a compound of the invention. In certain embodiments, more than one compound of Formula (I)-(VI), or a pharmaceutically acceptable salt thereof, is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the medical condition and the site of the medical condition.

In specific embodiments, it might be desirable to administer one or more of the compounds of Formula (I)-(VI), or a pharmaceutically acceptable salt thereof, locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer, tumor, or neoplastic or pre-neoplastic tissue.

In certain embodiments, it might be desirable to introduce one or more of the compounds of Formula (I)-(VI), or a pharmaceutically acceptable salt thereof, into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of Formula (I)-(VI), or pharmaceutically acceptable salts thereof, can be formulated as a suppository, with traditional binders and carriers such as triglycerides.

In another embodiment, the compounds of Formula (I)-(VI), or pharmaceutically acceptable salts thereof, can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of Formula (I)-(VI), or pharmaceutically acceptable salts thereof, can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the compound of the invention, e.g., the brain, thus, requiring only a fraction of the systemic dose (see, e.g., Goodson, in Medical Applications of Controlled Release, supra, vol. 2, pp. 115-138 (1984)). Other controlled-release systems are discussed in the review by Langer (Science 249:1527-1533 (1990)) can be used.

The present pharmaceutical compositions will contain an effective amount of the compounds of Formula (I)-(VI), or pharmaceutically acceptable salts thereof, preferably in purified form, together with a suitable amount of a pharmaceutically acceptable carrier so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating, and coloring agents can be used. When administered to a patient, the pharmaceutically acceptable carriers are preferably sterile. When the pharmaceutically acceptable carrier is water or an aqueous base the water or aqueous base is sterile. Water is a preferred carrier when the compounds of Formula (I)-(VI), or pharmaceutically acceptable salts thereof, are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present pharmaceutical compositions, if desired, can also contain minor amounts of wetting or emulsifying agents, or pH buffering agents.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

In a preferred embodiment, the compounds of Formula (I)-(VI), or pharmaceutically acceptable salts thereof, are formulated in accordance with routine procedures as a pharmaceutical composition adapted for intravenous administration to human beings. Typically, the compounds of Formula (I)-(VI), or pharmaceutically acceptable salts thereof, for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compounds of Formula (I)-(VI), or pharmaceutically acceptable salts thereof, are to be administered by infusion, they can be dispensed, for example, with an infusion bottle containing sterile pharmaceutical grade water or saline. Where the compounds of Formula (I)-(VI), or pharmaceutically acceptable salts thereof, are administered by injection, an ampule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administering the present compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard carriers such as mannitol, lactose, starch, magnesium stearate, sodium saccharine, cellulose, and magnesium carbonate.

The amount of the compound of Formula (I)-(VI), or a pharmaceutically acceptable salt thereof, that will be effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges are generally about 0.1 milligrams to about 250 milligrams, preferably, about 1 mg to about 100 mg and, more preferably, about 5 mg to about 50 mg. wherein each dose can be given 1 to 6 times a day, preferably 1 to 4 times per day. Effective doses can be extrapolated from dose-response curves derived from in vitro or animal model test systems. Such animal models and systems are well known in the art.

The invention also provides pharmaceutical packs or kits comprising one or more containers filled with one or more of the present compounds. Optionally associated with such container(s) can be a notice in the form prescribed by a governmental agency regulating the manufacture, use, or sale of pharmaceuticals or biological products, which notice reflects approval by the agency of manufacture for use or sale for human administration.

The present compounds of Formula (I)-(VI), or pharmaceutically acceptable salts thereof, are preferably assayed in vitro, and then in vivo, for the desired therapeutic or prophylactic activity, prior to use in humans. For example, in vitro assays can be used to determine whether administration of a specific compound or combination of the compounds of Formula (I)-(VI), or pharmaceutically acceptable salts thereof, is preferred. The compounds of Formula (I)-(VI), or pharmaceutically acceptable salts thereof, can also be demonstrated effective and safe using animal model systems.

5.7 EXAMPLES

5.7.1 Example

Synthesis of Compound CC

To a suspension of 3.0 g of 1-aminoanthraquinone in 45 mL of DMSO was added 9 g of ammonium thiocyanate. The reaction mixture was then heated to 50° C. and 15 mL of sulfuric acid added dropwise (exothermic reaction). The reaction mixture was then allowed to stir at room temperature for 16 hours. After stirring, 300 mL of water were added to the reaction mixture and the resulting suspension was filtered and dried in a vacuum oven to provide a crude product. The above procedure was then repeated using the crude product in place of 1-aminoanthraquinone. The resulting crude thiocyanate-addition intermediate was then recrystallized with o-dichlorobenzene (total volume 250 mL) to provide 1.9 g of a thiocyanate-addition intermediate. The structure of the thiocyanate-addition intermediate was confirmed by $^1$H NMR and electrospray mass spectrometry. $^1$H NMR (DMSO-$d_6$): 8.19 (dd, 1H), 8.14 (dd, 1H), 7.93 (dt, 1H), 7.86 (dt, 1H), 7.81 (d, 1H), 7.43 (d, 1H). ES-MS (m/z) 281 [M+1]$^+$.

A suspension of 300 mg of the thiocyanate-addition intermediate in 25 mL of liquid ammonia was heated to 140° C. in a bomb for 5 hours, the reaction mixture was diluted with 300 mL of water, and the reaction mixture was filtered to provide a final crude product. The final crude product was then purified using preparative HPLC (5 cm YMC C-18 column operated at a flow rate of 60 ml/min with a gradient elution from 40% aqueous acetonitrile with 0.1% trifluoroacetic acid to 100% acetonitrile with 0.1% trifluoroacetic acid over 20 minutes) to provide 55 mg of Compound CC. The structure of Compound CC was confirmed by $^1$H NMR and electrospray mass spectrometry. $^1$H NMR (DMSO-$d_6$): 8.49 (d, 1H), 8.39 (d, 1H), 8.29 (d, 1H), 7.89 (t, 1H), 7.78 (t, 1H), 7.28 (d, 1H). ES-MS (m/z) 253 [M+1]$^+$.

5.7.2 Example

Synthesis of Compound HD

A solution of compound CC in water/sulfuric acid was heated to 180° C. overnight to give the named compound. $^1$H NMR (DMSO-$d_6$): 8.23 (d, 2H), 7.91 (pent, 2H), 7.76 (d, 1H), 7.22 (d, 1H). ES-MS (m/z) 254 [M+1]$^+$.

5.7.3 Example

Synthesis of Compound CH

To a solution of compound CC (30 mg, 0.012 mmol) in pyridine (5 mL) was added acetyl chloride (10 μL, 0.14 mmol). After stirring at room temperature overnight, water was added and the product recovered by filtration (28 mg). $^1$H NMR (DMSO-$d_6$): 11.95 (s, 1H), 8.95 (d, 1H), 8.55 (d, 1H), 8.38 (d, 1H), 8.26 (d, 1H), 7.91 (t, 1H), 7.77 (t, 1H), 2.30 (s, 3H). ES-MS (m/z) 295 [M+1]$^+$.

5.7.4 Example

Synthesis of Compound HE

Compound HE was prepared according to the methodology of compound CH. $^1$H NMR (DMSO-$d_6$): 13.1 (s, 1H), 9.23 (d, 1H), 8.71 (d, 1H), 8.48 (d, 1H), 8.42 (d, 1H), 8.13 (d, 2H), 7.96 (t, 1H), 7.82 (t, 1H), 7.72 (m, 3H). ES-MS (m/z) 357 [M+1]$^+$.

5.7.5 Example

Synthesis of Compound HF

Compound HF was prepared according to the methodology of compound CH. $^1$H NMR (DMSO-$d_6$): 12.1 (s, 1H), 8.97 (d, 1H), 8.60 (d, 1H), 8.43 (d, 1H), 8.34 (d, 1H), 7.94 (t, 1H), 7.80 (t, 1H), 3.62 (s, 3H), 2.90 (t, 2H), 2.71 (t, 2H). ES-MS (m/z) 367 [M+1]$^+$.

5.7.6 Example

Synthesis of Compound HG

Compound HG was prepared according to the methodology of compound CH. $^1$H NMR (DMSO-$d_6$): 13.1 (s, 1H), 9.29 (s, 1H), 9.18 (d, 1H), 8.90 (d, 1H), 8.73 (d, 1H), 8.45 (m, 3H), 7.97 (t, 1H), 7.82 (t, 1H), 7.74 (m, 1H). ES-MS (m/z) 357 [M+1]$^+$.

5.7.7 Example

Biological Activity of Compound CC

JNK Assay:
To 10 μL of Compound (CC) in 20% DMSO/80% dilution buffer containing of 20 mM HEPES (pH 7.6), 0.1 mM EDTA, 2.5 mM magnesium chloride, 0.004% Triton×100, 2 μg/mL leupeptin, 20 mM β-glycerolphosphate, 0.1 mM sodium vanadate, and 2 mM DTT in water was added 30 μL of 50-200 ng His6-JNK1, JNK2, or JNK3 in the same dilution buffer. The mixture was pre-incubated for 30 minutes at room temperature. Sixty microliter of 10 μg GST-c-Jun(1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05%

Triton×100, 11 μM ATP, and 0.5 μCi γ-32P ATP in water was added and the reaction was allowed to proceed for 1 hour at room temperature. The c-Jun phosphorylation was terminated by addition of 150 μL of 12.5% trichloroacetic acid. After 30 minutes, the precipitate was harvested onto a filter plate, diluted with 50 μL of the scintillation fluid and quantified by a counter. The $IC_{50}$ values were calculated as the concentration of Compound (CC) at which the c-Jun phosphorylation was reduced to 50% of the control value. Compounds that inhibit JNK preferably have an $IC_{50}$ value ranging 0.01-10 μM in this assay. Compound (CC) has an $IC_{50}$ according to this assay of 1 μM for JNK2 and 400 nM for JNK3. The measured $IC_{50}$ value for Compound CC, as measured by the above assay, however, shows some variability due to the limited solubility of Compound CC in aqueous media. Despite the variability, however, the assay consistently does show that Compound CC inhibits JNK. This assay demonstrates that Compound (CC), illustrative of the present compounds, inhibits JNK2 and JNK3 and, accordingly, is useful for treating or preventing a disorder alleviated by modulating JNK, preferably by inhibiting JNK.

Selectivity for JNK:

Compound (CC) was also assayed for its inhibitory activity against several protein kinases, listed below, using techniques known to those skilled in art (See, e.g., Protein Phosphorylation, Sefton & Hunter, Eds., Academic Press, pp. 97-367, 1998). The following $IC_{50}$ values were obtained:

| Enzyme | $IC_{50}$ |
| --- | --- |
| p38-2 | >30,000 nM |
| MEK6 | >30,000 nM |
| LKK1 | >30,000 nM |
| IKK2 | >30,000 nM |

This assay shows that Compound (CC), illustrative of the present compounds, selectively inhibits JNK relative to other protein kinases and, accordingly, is a selective JNK inhibitor. Therefore, Compound (CC) is useful for selectively treating or preventing a disorder alleviated by modulating JNK, preferably by inhibiting JNK.

Jurkat T-Cell IL-2 Production Assay:

Jurkat T cells (clone E6-1) were purchased from the American Type Culture Collection of Manassas, Va. and maintained in growth media consisting of RPMI 1640 medium containing 2 mM L-glutamine (commercially available from Mediatech Inc. of Herndon, Va.), with 10% fetal bovine serum (commercially available from Hyclone Laboratories Inc. of Omaha, Nebr.) and penicillin/streptomycin. All cells were cultured at 37° C. in 95% air and 5% $CO_2$. Cells were plated at a density of $0.2\times10^6$ cells per well in 200 μL of media. Compound stock (20 mM) was diluted in growth media and added to each well as a 10× concentrated solution in a volume of 25 μL, mixed, and allowed to pre-incubate with cells for 30 minutes. The compound vehicle (dimethylsulfoxide) was maintained at a final concentration of 0.5% in all samples. After 30 minutes the cells were activated with PMA (phorbol myristate acetate, final concentration 50 ng/mL) and PHA (phytohemagglutinin, final concentration 2 μg/mL). PMA and PHA were added as a 10× concentrated solution made up in growth media and added in a volume of 25 μL per well. Cell plates were cultured for 10 hours. Cells were pelleted by centrifugation and the media removed and stored at −20° C. Media aliquots are analyzed by sandwich ELISA for the presence of IL-2 as per the manufacturers instructions (Endogen Inc. of Woburn, Mass.). The $IC_{50}$ values were calculated as the concentration of Compound (CC) at which the IL-2 production was reduced to 50% of the control value. Compounds that inhibit JNK preferably have an $IC_{50}$ value ranging from 0.1-30 μM in this assay. Compound (CC) has an $IC_{50}$ of 30 μM. The measured $IC_{50}$ value for Compound CC, as measured by the above assay, however, shows some variability due to the limited solubility of Compound CC in aqueous media. Despite the variability, however, the assay consistently does show that Compound CC inhibits JNK.

This assay shows that Compound (CC), illustrative of the present compound, inhibits IL-2 production in Jurkat T-cells and accordingly inhibits JNK. Therefore, Compound (CC) is useful for selectively treating or preventing a disorder alleviated by modulating JNK, preferably by inhibiting JNK.

[$^3$H]Dopamine Cell Culture Assay:

Cultures of dopaminergic neurons were prepared according to a modification of the procedure described by Raymon and Leslie (J. Neurochem. 62, 1015-1024, 1994). Timemated pregnant rats were sacrificed on embyronic day 14-15 (crown rump length 11-12 mm) and the embryos removed by cesarean section. The ventral mesencephalon, containing the dopaminergic neurons, was dissected from each embryo. Tissue pieces from approximately 48 embryos were pooled and dissociated both enzymatically and mechanically. An aliquot from the resulting cell suspension was counted and the cells were plated in high glucose DMEM/F12 culture medium with 10% fetal bovine serum at a density of $1\times10^5$ cells/well of a Biocoat poly-D-lysine-coated 96-well plate. The day following plating was considered 1 day in vitro (DIV). Cells were maintained in a stable environment at 37° C., 95% humidity, and 5% $CO_2$. A partial medium change was performed at 3 DIV. At 7 DIV, cells were treated with the neurotoxin, 6-hydroxydopamine (6-OHDA, 30 μM) in the presence and absence of Compound CC. Cultures were processed for [$^3$H]dopamine uptake 22 hours later.

[$^3$H]Dopamine uptake is used as a measure of the health and integrity of dopaminergic neurons in culture (Prochiantz et al., PNAS 76: 5387-5391, 1979). It was used in these studies to monitor the viability of dopaminergic neurons following exposure to the neurotoxin 6-OHDA. 6-OHDA has been shown to damage dopaminergic neurons both in vitro and in vivo and is used to model the cell death observed in Parkinson's disease (Ungerstedt, U., Eur. J. Pharm., 5 (1968) 107-110 and Hefti et al., Brain Res., 195 (1980) 123-137). Briefly, cells treated with 6-OHDA in the presence and absence of Compound CC were assessed in the uptake assay 22 hrs after exposure to 6-OHDA. Culture medium was removed and replaced with warm phosphate buffered saline (PBS) with calcium and magnesium, 10 μM pargyline, 1 mM ascorbic acid, and 50 nM [$^3$H]dopamine. Cultures were incubated at 37° C. for 20 min. Radioactivity was removed and the cultures were washed 3× with ice cold PBS. To determine the intracellular accumulation of [$^3$H] dopamine, cells were lysed with M-PER detergent and an aliquot was taken for liquid scintillation counting. The measured effect of Compound CC on the intracellular accumulation of [$^3$H]dopamine, as measured by the above assay, however, shows some variability due to the limited solubility of Compound CC in aqueous media. Despite the variability, however, the assay consistently does show that Compound CC protects rat ventral mesencephalan neurons from the toxic effects of 6-OHDA As shown in FIG. 1, Compound CC, at a concentration of approximately $3\times10^{-6}$ M, protects rat ventral mesencephalan neurons from the toxic effects of 6-OHDA. Despite the variability discussed above, the assay consistently does show that Compound CC protects rat ventral mesencephalan neurons from the toxic effects of 6-OHDA Accordingly, Compound CC, illustrative of the present compounds, is useful for treating or preventing Parkinson's disease.

5.7.8 Example

Brain-Blood Plasma Distribution of Compound CC In Vivo

Compound CC was administered intravenously (10 mg/kg) into the veins of Sprague-Dawley rats. After 2 hr, blood samples were obtained from the animals and their vascular systems were perfused with approximately 100 mL of saline to rid their brains of blood. The brains were removed from the animals, weighed, and homogenized in a 50 mL conical tube containing 10 equivalents (w/v) of methanol/saline (1:1) using a Tissue Tearer (Fischer Scientific). The homogenized material was extracted by adding 600 μL of cold methanol to 250 μL of brain homogenate vortexed for 30 sec and subjected to centrifugation for 5 min. After centrifugation, 600 μL of the resulting supernatant was transferred to a clean tube and evaporated at room temperature under reduced pressure to provide a pellet. The resulting pellet was reconstituted in 250 μL of 30% aqueous methanol to provide a brain homogenate analysis sample. A plasma analysis sample was obtained using the brain homogenate analysis sample procedure described above by substituting plasma for brain homogenate. Standard plasma samples and standard brain homogenate samples containing known amounts of Compound CC were also prepared by adding 5 μL of serial dilutions (50:1) of a solution of Compound CC freshly prepared in cold ethanol to 250 μL of control rat plasma (Bioreclamation of Hicksville, N.Y.) or control brain homogenate. The standard plasma samples and standard brain homogenate samples were then subjected to the same extraction by protein precipitation, centrifugation, evaporation, and reconstitution procedure used for the brain homogenate to provide brain homogenate standard analysis samples and plasma standard analysis samples. The brain homogenate analysis samples, plasma analysis samples, and standard analysis samples were analyzed and compared using HPLC by injecting 100 μL of a sample onto a 5 μm C-18 Luna column (4.6 mm×150 mm, commercially available from Phenomenex of Torrance, Calif.) and eluting at 1 mL/min with a linear gradient of 30% aqueous acetonitrile containing 0.1% trifluoroacetic acid to 90% aqueous acetonitrile containing 0.1% trifluoroacetic acid over 8 minutes and holding at 90% aqueous acetonitrile containing 0.1% trifluoroacetic acid for 3 min. with absorbance detection at 450 nm. Recovery of Compound CC was 56±5.7% for plasma and 42±6.2% for the brain. The concentration of Compound CC in the brain and plasma was determined by comparing HPLC chromatograms obtained from the brain homogenate analysis samples and plasma analysis samples to standard curves constructed from analysis of the brain homogenate standard analysis samples and the plasma standard analysis samples, respectively. Results from this study show that Compound CC, following intravenous administration, crosses the blood-brain barrier to a significant extent. In particular, brain-drug concentrations were approximately 65 nmole/g and plasma concentrations were approximately 7 μM at 2 hr post-dose, resulting in a brain-plasma concentration ratio of approximately 9-fold (assuming 1 g of brain tissue is equivalent to 1 mL of plasma). This example shows that Compound CC, illustrative of the present compounds, has enhanced ability to cross the blood-brain barrier. In addition, this example shows that the present compounds, in particular Compound CC, when administered to a patient can cross the blood-brain barrier.

It will be appreciated that, although specific embodiments of the invention have been described herein for purposes of illustration, the invention described and claimed herein is not to be limited in scope by the specific embodiments herein disclosed. These embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references have been cited, the entire disclosure of which are incorporated herein by reference.

What is claimed is:

1. A compound having the formula:

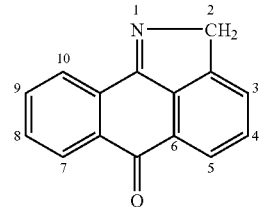

or a pharmaceutically acceptable salt thereof, being (i) unsubstituted, (ii) monosubstituted and having a first substituent, or (iii) disubstituted and having a first substituent and a second substituent;

the first or second substituent, when present, being at the 3, 4, 5, 7, 8, 9, or 10 position;

the first and second substituent, when present, are independently alkyl, halogen, nitro, trifluoromethyl, sulfonyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

(a)

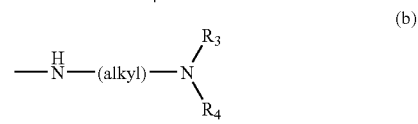

(b)

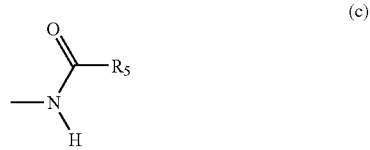

(c)

-continued (d)
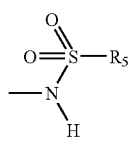

(e)
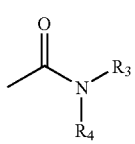

(f)
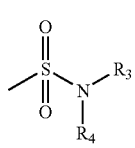

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, monoalkylamino, di-alkylamino, arylamino, arylalkylamino, cycloalkylamino, cycloalkylalkylamino, aminoalkyl, mono-alkylaminioalkyl, or di-alkylaminoalkyl.

2. The compound of claim 1, wherein the first or second substituent are present at the 5, 7, or 9 position.

3. The compound of claim 2, wherein the first and second substituent are independently alkoxy, aryloxy, aminoalkyl, mono-alkylaminoalkyl, di-alkylaminoalkyl, or a group represented by the formula (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonyl or cycloalkylalkyl.

4. A pharmaceutical composition comprising a compound, or a pharmaceutically acceptable salt of the compound, having the formula:

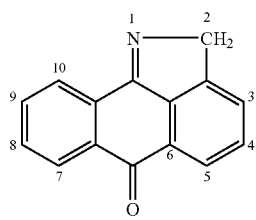

or a pharmaceutically acceptable salt thereof,
being (i) unsubstituted, (ii) monosubstituted and having a first substituent, or (iii) disubstituted and having a first substituent and a second substituent;

the first or second substituent, when present, being at the 3, 4, 5, 7, 8, 9, or 10 position;

the first and second substituent, when present, are independently alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, monoalkylaminoalkoxy, di-alkylaminoalkoxy, or a group represented by formula (a), (b), (c), (d), (e), or (f):

(a)
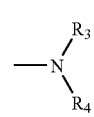

(b)
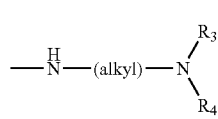

(c)
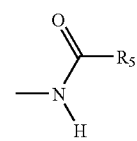

(d)
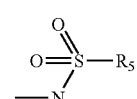

(e)
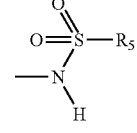

(f)
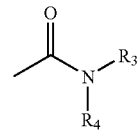

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, amino, monoalkylamino, di-alkylamino, arylamino, arylalkylamino, cycloalkylamino, cycloalkylalkylamino, aminoalkyl, mono-alkylaminioalkyl, or di-alkylaminoalkyl;

and a pharmaceutically acceptable carrier or vehicle.

* * * * *